US005112819A

United States Patent [19]

Ross et al.

[11] Patent Number: 5,112,819

[45] Date of Patent: May 12, 1992

[54] IMIDAZOLE DERIVATIVES, PHARMACEUTICAL COMPOSITIONS AND USE

[75] Inventors: Barry C. Ross, Luton; Barrie E. Kirk, Ickenham; Michael G. Lester, Rickmansworth; Panayiotis A. Procopiou, Harrow; Nigel S. Watson, Chalfont St. Giles, all of England

[73] Assignee: Glaxo Group Limited, London, England

[21] Appl. No.: 593,954

[22] Filed: Oct. 9, 1990

[30] Foreign Application Priority Data

Oct. 10, 1989 [GB] United Kingdom ................. 8922767
Mar. 30, 1990 [GB] United Kingdom ................. 9007155

[51] Int. Cl.$^5$ .................. C07D 223/04; C07D 233/64; A61K 31/55; A61K 31/415

[52] U.S. Cl. .................................... 514/212; 514/326; 514/397; 514/400; 540/603; 546/210; 548/336; 548/342

[58] Field of Search ................ 548/336, 342; 540/603; 514/397, 212, 316, 326, 400; 546/187, 210

[56] References Cited

U.S. PATENT DOCUMENTS

| | | | |
|---|---|---|---|
| 4,647,576 | 3/1987 | Hoefle et al. | 514/422 |
| 4,668,794 | 5/1987 | Wareing | 548/342 |
| 4,755,606 | 7/1988 | Wareing | 548/110 |
| 4,808,607 | 2/1989 | Wareing | 548/336 |
| 4,829,081 | 5/1989 | Damon, II et al. | 514/438 |
| 4,851,427 | 7/1989 | Wareing | 514/422 |
| 4,870,199 | 9/1989 | Chen et al. | 556/437 |
| 4,927,851 | 5/1990 | Damon, II et al. | 514/460 |
| 4,946,841 | 8/1990 | Baader et al. | 514/247 |
| 5,013,749 | 5/1991 | Watson et al. | 548/336 |

FOREIGN PATENT DOCUMENTS

| | | |
|---|---|---|
| 0221025 | 5/1987 | European Pat. Off. . |
| 0244364 | 11/1987 | European Pat. Off. . |
| 0324347 | 7/1989 | European Pat. Off. . |
| 0334014 | 9/1989 | European Pat. Off. . |
| WO86/07054 | 12/1986 | PCT Int'l Appl. . |
| 2205838A | 12/1988 | United Kingdom . |

*Primary Examiner*—Mary C. Lee
*Assistant Examiner*—Lenora Miltenberger
*Attorney, Agent, or Firm*—Bacon & Thomas

[57] ABSTRACT

Certain novel imidazole derivatives N-substituted by a vinyl group itself carrying a mevalonic acid derivative or corresponding lactone are inhibitors of HMG-CoA reductase and are useful for lowering blood plasma cholesterol levels.

The compounds are of general formula (I):

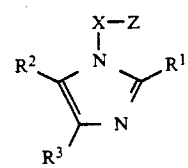

(I)

in which one of the groups $R^1$ and $R^2$ represents a $C_{1-6}$alkyl group optionally substituted by one to three halogen atoms and the other represents a phenyl ring optionally substituted by one to five substituents selected from halogen atoms and hydroxyl, $C_{1-3}$alkyl, $C_{1-3}$alkoxy, $S(O)_nC_{1-3}$alkyl, $(CH_2)_mNR^aR^b$, $(CH_2)_mNR^cCOR^d$ and trifluoromethyl groups;

$R^3$ represents a phenyl ring optionally substituted by one to five substituents selected from halogen atoms and hydroxyl, $C_{1-3}$alkyl, $C_{1-3}$alkoxy, $S(O)_nC_{1-3}$alkyl, $(CH_2)_mNR^aR^b$, $(CH_2)_mNR^cCOR^d$ and trifluoromethyl groups; with the proviso that at least one of the groups $R^1$, $R^2$ and $R^3$ contains an $S(O)_nC_{1-3}$alkyl, $(CH_2)_mNR^aR^b$ or $(CH_2)_mNR^cCOR^d$ substituent;

X represents —CH=CH—;

Z represents

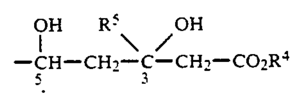

(or)

(a)

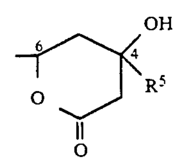

(b)

and physiologically acceptable solvates, physiologically acceptable acid addition salts thereof when $R^4$ represents hydrogen or a physiologically acceptable and metabolically labile carboxyl protecting group when Z is (a), and quaternary ammonium derivatives thereof.

13 Claims, No Drawings

IMIDAZOLE DERIVATIVES, PHARMACEUTICAL COMPOSITIONS AND USE

This invention relates to imidazole derivatives having hypocholesterolemic and hypolipidemic activity, to processes for their preparation, to pharmaceutical compositions containing them and to their use in medicine, particularly in the treatment and/or prevention of atherosclerosis and coronary heart disease.

High levels of blood cholesterol and blood lipids are conditions which are involved in the onset of vessel wall disease. 3-Hydroxy-3-methylglutaryl-coenzyme A (HMG—CoA) reductase is the rate-limiting enzyme in cholesterol biosynthesis and it is well known that inhibitors of this enzyme are effective in lowering the level of blood plasma cholesterol, especially low density lipoprotein cholesterol (LDL-C). It has now been established that lowering LDL-C levels affords protection from coronary heart disease.

Derivatives of mevalonic acid and the corresponding lactones are known to inhibit HMG—CoA reductase, for example Monaghan et al. reported (U.S. Pat. No. 4,231,938) the formation of the mevalonolactone analogue mevinolin (now known as lovastatin) by the cultivation of a microfungus of the genus Aspergillus and that this product was a potent inhibitor of cholesterol biosynthesis.

More recently, PCT Patent Specification No. WO 8607054 discloses C-linked imidazole derivatives useful for treating hyperlipoproteinaemia and atherosclerosis, which have the following formula:

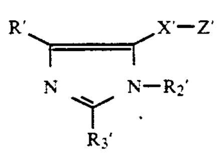

where X' represents a $C_{1-3}$ saturated or unsaturated alkylene chain; Z' represents inter alia a group of formula (a)

$-CH(OH)-CH_2-C(R_{13}')(OH)-CH_2-CO_2R_{14}'$ or (b)

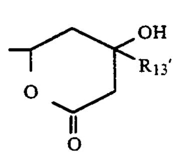

where $R'_{13}$ is hydrogen or $C_{1-3}$alkyl and $R'_{14}$ is hydrogen, an ester group or a cation; and $R'_1$, $R'_2$ and $R'_3$ represent inter alia $C_{1-6}$alkyl or optionally substituted phenyl.

U.S. Pat. No. 4,647,576 disclosed N-substituted pyrroles, useful as hypolipidaemic and hypocholesterolaemic agents, which have the formula

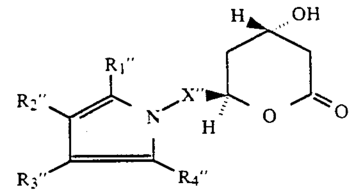

and the corresponding dihydroxy acids thereof where X'' represents $-CH_2-$, $-CH_2CH_2-$ or $-CH(CH_3)-CH_2$; $R''_1$ represents inter alia $C_{1-4}$alkyl, optionally substituted phenyl or a pyridyl ring or N-oxide thereof; $R''_2$ and $R''_3$ represent inter alia hydrogen atoms, $CF_3$, $C_{1-4}$alkyl or a phenyl ring; and $R''_4$ represents inter alia $C_{1-4}$alkyl or $CF_3$.

Similarly, EP0221025 discloses inter alia C-substituted pyrroles for use as hypolipoproteinemic and antiatherosclerotic agents which have the formulae

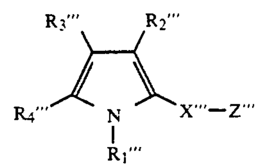

or

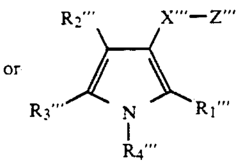

where $R_1'''$, $R_2'''$, $R_3'''$ and $R_4'''$ are independently $C_{1-4}$alkyl not containing an asymmetric carbon atom, $C_{3-7}$cycloalkyl or a ring

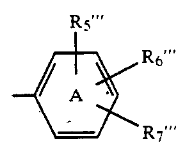

or in the case of $R_3'''$ and $R_4'''$ additionally hydrogen; each $R_5'''$, $R_6'''$ and $R_7'''$ are independently inter alia hydrogen or halogen atoms, alkyl, alkoxy or trifluoromethyl groups; X''' is $(CH_2)_m$ or $(CH_2)_qCH{=}CH(CH_2)_q$, m is 0, 1, 2 or 3 and both q's are 0 or one is 0 and the other is 1;

Z''' is

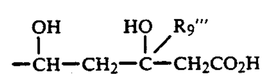

wherein $R_9'''$ is hydrogen or $C_{1-3}$alkyl, in free acid form or in the form of an ester, lactone or salt as appropriate.

According to the present invention there are provided certain novel imidazole derivatives which are potent inhibitors of cholesterol biosynthesis by virtue of their ability to inhibit the enzyme HMG—CoA reductase.

Thus, the invention provides compounds of the general formula (I):

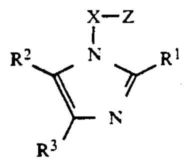
(I)

in which one of the groups $R^1$ and $R^2$ represents a $C_{1-6}$alkyl group optionally substituted by one to three halogen atoms and the other represents a phenyl ring optionally substituted by one to five substituents selected from halogen atoms and hydroxyl, $C_{1-3}$alkyl, $C_{1-3}$alkoxy, $S(O)_nC_{1-3}$alkyl, $(CH_2)_mNR^aR^b$, $(CH_2)_mNR^cCOR^d$ and trifluoromethyl groups;

$R^3$ represents a phenyl ring optionally substituted by one to five substituents selected from halogen atoms and hydroxyl, $C_{1-3}$alkyl, $C_{1-3}$alkoxy, $S(0)_nC_{1-3}$alkyl, $(CH_2)_mNR^aR^b$, $(CH_2)_mNR^cCOR^d$ and trifluoromethyl groups; with the proviso that at least one of the groups $R^1$, $R^2$ and $R^3$ contains an $S(O)_nC_{1-3}$alkyl, $(CH_2)_mNR^aR^b$ or $(CH_2)_mNR^cCOR^d$ substituent;

X represents —CH=CH—;

Z represents

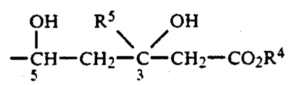
(or) (a)

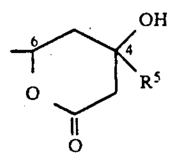
(b)

m represents zero, 1,2,3 or 4;

n represents zero, 1 or 2;

$R^a$ and $R^b$, which may be the same or different, each represent a hydrogen atom, a $C_{1-4}$alkyl group, a saturated monocyclic 5 to 7 membered ring or together with the nitrogen atom to which they are attached form a saturated monocyclic 5 to 7 membered ring;

$R^c$ represents a hydrogen atom or a $C_{1-4}$alkyl group;

$R^d$ represents a hydrogen atom, a $C_{1-4}$alkyl group or a $C_{1-4}$alkoxy group;

$R^4$ represents a hydrogen atom, a physiologically acceptable and metabolically labile carboxyl protecting group or a physiologically acceptable cation; and $R^5$ represents a hydrogen atom or a $C_{1-3}$alkyl group;

and physiologically acceptable solvates, physiologically acceptable acid addition salts thereof when $R^4$ represents hydrogen or a physiologically acceptable and metabolically labile carboxyl protecting group when Z is (a), and quaternary ammonium derivatives thereof.

Physiologically acceptable acid addition salts of the compounds of formula (I) include those derived from physiologically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves physiologically acceptable, may be useful in the preparation of salts useful as intermediates in obtaining the compounds of the invention and their physiologically acceptable acid addition salts.

References hereinafter to a compound according to the invention includes both compounds of formula (I) and their physiologically acceptable acid addition salts together with physiologically acceptable solvates and, where appropriate, quaternary ammonium derivatives.

References hereinafter to compounds of formula (I) and physiologically acceptable derivatives thereof includes compounds of formula (I) and their physiologically acceptable solvates, physiologically acceptable acid addition salts and quaternary ammonium derivatives.

It will be appreciated that compounds of formula (I) possess at least two asymmetric carbon atoms namely the two carbon atoms (numbered 3 and 5) bearing the hydroxy groups in formula (a) and the carbon atom (numbered 4) bearing the group $R^5$ and the carbon atom (numbered 6) attached to X in formula (b) above.

In addition, in the compounds of formula (I) X may be

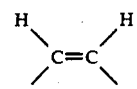

i.e. in the (Z) configuration, or X may be

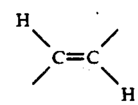

i.e. in the (E) configuration.

The compounds according to the invention thus include all stereoisomers and mixtures thereof, including the racemates.

In the compounds of formula (I) where Z represents a group of formula (a) the two diastereoisomeric pairs resulting from the two centres of asymmetry are hereinafter referred to as the threo and erythro isomers, threo and erythro referring to the relative configuration of the two hydroxy groups in the 3- and 5-positions.

In the compounds of formula (I) where Z represents a group of formula (b) the two diastereoisomeric pairs resulting from the two centres of asymmetry are hereinafter referred to as the cis and trans isomers, cis and trans referring to the relative configuration of the hydrogen atom and the group $R^5$ in the 6- and 4-positions respectively. In the threo and cis isomers of the compounds of the invention the two asymmetric carbon atoms each have the same absolute configuration and thus the term threo and/or cis includes the R,R and S,S enantiomers and mixtures thereof including the racemates.

In the erythro and trans isomers of the compounds of the invention the two asymmetric carbon atoms have different absolute configurations and thus the term erythro and/or trans includes the R,S and S,R enantiomers and mixtures thereof including the racemates.

In the general formula (I) the phenyl groups represented by $R^1$, $R^2$ and $R^3$ may for example contain one to five substituents, which may be present at the 2-, 3-, 4-, 5- or 6- positions on the phenyl ring. When $R^1$, $R^2$ and $R^3$ contain halogen atoms these may be fluorine, chlorine, bromine and iodine atoms.

In the compounds of general formula (I), the term 'alkyl' as a group or part of a group means that the group is straight or branched and may be for example a methyl, ethyl, n-propyl, isopropyl, n-butyl, isobutyl, tertbutyl, n-pentyl or n-hexyl group. Similarly 'alkoxy' may represent methoxy, ethoxy, n-propoxy, isopropoxy, n-butoxy, isobutoxy or tertbutoxy.

In the compounds of formula (I) $R^1$, $R^2$ and $R^3$ may represent a phenyl ring substituted by a group $S(O)_n$-$C_{1-3}$alkyl and examples of this group include $S(O)_n$-methyl, $S(O)_n$ethyl, $S(O)_n$n-propyl and $S(O)_n$isopropyl where n is zero, one or two (e.g. —$SCH_3$ and $S(O)_2CH_3$). Other phenyl ring substituents include the group $(CH_2)_mNR^aR^b$ where $R^a$ and $R^b$ may each represent a hydrogen atom or a $C_{1-4}$ alkyl (e.g. methyl, ethyl, n-propyl, isopropyl, n-butyl, isobutyl or tertbutyl) group and m represents 0–4 (e.g. —$NH_2$, —NHMe, —$CH_2$NHMe, —$NMe_2$ and —$NEt_2$). $R^a$ and $R^b$ may also both represent a saturated monocyclic 5 to 7 membered ring (e.g. cyclopentyl, cyclohexyl or cycloheptyl) for example the group $NR^aR^b$ may represent —NH-$C_6H_{11}$ or —NMe—$C_6H_{11}$. When the group $NR^aR^b$ forms a ring this may be, for example, a pyrrolidino, piperidino or hexamethylenimino ring. Also included are the phenyl ring substituents $(CH_2)_mNR^cCOR^d$ where m represents 0–4 and $R^c$ and $R^d$ may each represent a hydrogen atom or a $C_{1-4}$alkyl (e.g. methyl, ethyl, n-propyl, isopropyl, n-butyl, isobutyl or tertbutyl) group (e.g. $NHCOCH_3$) or $R^d$ may additionally represent a $C_{1-4}$alkoxy (e.g. methoxy, ethoxy, n-propoxy, isopropoxy, n-butoxy, isobutoxy or tertbutoxy) group (e.g. NHCO.OC$(CH_3)_3$).

Compounds of formula (I) wherein $R^1$, $R^2$ or $R^3$ represents a phenyl ring substituted by the group $(CH_2)_mNR^aR^b$, where $R^a$ and $R^b$ are other than hydrogen, are capable of forming quaternary ammonium derivatives.

Suitable quaternary ammonium derivatives include for example those derivatives formed by reacting a suitable compound of formula (I) with a quarternising reagent such as $R^e$—L (where $R^e$ represents a $C_{1-4}$alkyl group and L represents a suitable leaving group for example a halogen atom) according to conventional methods.

In the substituent groups $(CH_2)_mNR^aR^b$ and $(CH_2)_mNR^cCOR^d$ the alkylene chain $(CH_2)_m$ includes both branched and unbranched alkylene groups. Thus $(CH_2)_m$ may represent a $C_{1-4}$alkylene chain optionally substituted by one or more $C_{1-3}$alkyl groups.

When any of the groups $R^1$, $R^2$ or $R^3$ represents a phenyl group substituted by one or more substituents other than the sulphur and nitrogen containing substituents $S(O)_nC_{1-3}$alkyl, $(CH_2)_mNR^aR^b$ and $(CH_2)_mNR^cCOR^d$ examples of such substituents may be selected from fluorine, chlorine, bromine or iodine atoms or methyl, ethyl, n-propyl, isopropyl, methoxy, ethoxy, n-propoxy, isopropoxy, trifluoromethyl or hydroxy groups. The terms "alkyl" and "alkoxy" when referred to hereinafter as suitable substituents contained within the definitions of $R^1$, $R^2$ and $R^3$ relate to $C_{1-3}$alkyl and $C_{1-3}$alkoxy groups respectively unless otherwise specified.

Thus, for example, when any of $R^1$, $R^2$ or $R^3$ represents a monosubstituted phenyl group not containing the above sulphur and nitrogen containing substituents this may be a 2-halo, a 3-halo (e.g. 3-bromo or 3-chloro), a 4-halo (e.g. 4-chloro or 4-fluoro), a 2-alkyl, a 3-alkyl, a 4-alkyl (e.g. 4-methyl), a 2-alkoxy, a 3-alkoxy (e.g. 3-methoxy), a 4-alkoxy (e.g. 4-methoxy), a trifluoromethyl such as a 3-trifluoromethyl or 4-trifluoromethyl, or a hydroxy such as a 3-hydroxy or 4-hydroxy substituted phenyl group.

When any of $R^1$, $R^2$ or $R^3$ represents a disubstituted phenyl group not containing the above sulphur and nitrogen containing substituents this may be for example a dihalo such as a 2,3-dihalo, a 2,4-dihalo, a 2,5-dihalo, a 2,6-dihalo, a 3,4-dihalo or a 3,5-dihalo (e.g. 3,5-dibromo or 3,5-dichloro), a dialkyl such as a 2,3-dialkyl, a 2,4-dialkyl, a 2,5-dialkyl, a 3,4-dialkyl, a 3,5-dialkyl (e.g. 3,5-dimethyl), or an alkyl-halo such as a methyl-fluoro (e.g. 4-fluoro-2-methyl) or methyl-chloro (e.g. 5-chloro-2-methyl) substituted phenyl group.

When any of $R^1$, $R^2$ or $R^3$ represents a trisubstituted phenyl group not containing the above sulphur and nitrogen containing substituents this may be for example a dialkyl-halo such as a dimethyl-halo (e.g. 4-chloro-3,5-dimethyl or 3,5-dimethyl-4-fluoro) or diethyl-halo (e.g. 3,5-diethyl-4-fluoro) substituted phenyl group.

When any of $R^1$, $R^2$ or $R^3$ represents a substituted phenyl group this is prefrably a mono, -di-or trisubstituted phenyl group.

When any of $R^1$, $R^2$ or $R^3$ are substituted by the groups $S(O)_nC_{1-3}$alkyl, $(CH_2)_mNR^aR^b$ or $(CH_2)_mNR^cCOR^d$ then the phenyl rings are preferably monosubstituted and more preferably this substituent is in the 3-position.

In the compounds of formula (I) $R^1$ or $R^2$ may represent a $C_{1-6}$alkyl group optionally substituted by one, two or three fluorine, chlorine, bromine or iodine atoms, for example $R^1$ or $R^2$ may represent a $C_{1-4}$alkyl (e.g. a branched $C_{3-4}$alkyl such as an isopropyl) or a trifluoromethyl group.

In the compounds of formula (I) where Z represents a group of formula (a) and $R^4$ represents a physiologically acceptable cation this may include alkali metal (e.g. sodium or potassium) and alkaline earth metal (e.g. calcium or magnesium) cations.

It will be appreciated that salts formed with cations other than the aforementioned physiologically acceptable cations may find use, for example, in the preparation of compounds of formula (I) and such salts also form part of the invention.

Where $R^4$ represents a physiologically acceptable and metabolically labile carboxyl protecting group this may include for example the residue of an ester-forming aliphatic or araliphatic alcohol. Examples of such groups include lower alkyl groups such as $C_{1-4}$alkyl (e.g. methyl, ethyl, n-propyl, isopropyl, n-butyl, isobutyl, tertbutyl) groups and aralkyl (e.g. benzyl) groups. Other esters, while not in themselves physiologically acceptable, may find use in the preparation of other compounds of formula (I). In addition, compounds where $R^4$ represents an optically active ester group may find use in the separation of racemic mixtures.

$R^5$ in the general formula (I) may represent a hydrogen atom or a methyl, ethyl, n-propyl or isopropyl group.

A preferred group of compounds of formula (I) are those wherein $R^1$ represents a $C_{1-4}$alkyl group, more particularly an isopropyl group. Within this class of compounds a preferred group includes those compounds wherein $R^2$ is a substituted phenyl group, for example a phenyl group substituted by a fluorine atom, a group $S(O)_nC_{1-3}$alkyl, $(CH_2)_mNR^aR^b$ or a group $(CH_2)_mNR^cCOR^d$ and $R^3$ is a phenyl group substituted by for example a fluorine atom, a group $S(O)_nC_{1-3}$alkyl, $(CH_2)_mNR^aR^b$ or a group $(CH_2)_mNR^cCOR^d$. A particularly preferred group of compounds from within this class includes those compounds where $R^2$ represents a phenyl group substituted by a fluorine atom, and $R^3$ is a phenyl group substituted by a group $S(O)_nC_{1-3}$alkyl, $(CH_2)_mNR^aR^b$ or $(CH_2)_mNR^cCOR^d$.

A preferred group of compounds of formula (I) are those wherein $R^5$ represents a methyl group or more particularly a hydrogen atom.

When in the compounds of formula (I) Z represents the group (a) this is preferably in the erythro configuration as defined above, and when Z represents the group (b) then this is preferably in the trans configuration as defined above.

A preferred group of compounds of formula (I) wherein Z represents a group (a) are the erythro enantiomers having the 3R,5S configuration and mixtures containing said enantiomers including the racemates.

A preferred group of compounds of formula (I) wherein Z represents a group (b) are the trans enantiomers having the 4R,6S configuration and mixtures containing said enantiomers including the racemates.

A particularly preferred group of compounds of formula (I) are the 3R,5S enantiomers where Z represents a group (a) substantially free of the corresponding 3S, 5R enantiomers, and the 4R,6S enantiomers where Z represents a group (b) substantially free of the corresponding 4S, 6R enantiomers.

Compounds of formula (I) wherein X is in the (E) configuration as defined above are preferred.

Preferred compounds of the invention are (±)-trans-(E)-6-[2-[4-(3-aminophenyl)-5-(4-fluorophenyl)-2-(1-methylethyl)-1H-imidazol-1-yl]ethenyl]-4-hydroxy-tetrahydro-2H-pyran-2-one;

(±)-trans-(E)-6-[2-[4-(3-dimethylaminophenyl)-5-(4-fluorophenyl)-2-(1-methylethyl)-1H-imidazol-1-yl]ethenyl]-4-hydroxy-tetrahydro-2H-pyran-2-one;

(±)-trans-(E)-6-[2-[5-(4-fluorophenyl)-2-(1-methylethyl)-4-[(3-methylthio)phenyl]-1H-imidazol-1-yl]ethenyl]-4-hydroxy-tetrahydro-2H-pyran-2-one;

(±)-trans-(E)-6-[2-[5-(4-fluorophenyl)-2-(1-methylethyl)-4-[(3-methylsulphonyl)phenyl]-1H-imidazol-1-yl]ethenyl]-4-hydroxy-tetrahydro-2H-pyran-2-one;

(±)-trans-(E)-6-[2-[4-(3-acetamidophenyl)-5-(4-fluorophenyl)-2-(1-methylethyl)-1H-imidazol-1-yl]ethenyl]-4-hydroxy-tetrahydro-2H-pyran-2-one;

(±)-trans-(E)-6-[2-[4-(3-cyclohexylaminophenyl)-5-(4-fluorophenyl)-2-(1-methylethyl)-1H-imidazol-1-yl]ethenyl]-4-hydroxy-tetrahydro-2H-pyran-2-one;

(±)-trans-(E)-6-[2-[4-(3-diethylaminophenyl)-5-(4-fluorophenyl)-2-(1-methylethyl)-1H-imidazol-1-yl]ethenyl]-4-hydroxy-tetrahydro-2H-pyran-2-one;

(±)-trans-(E)-6-[2-[5-(4-fluorophenyl)-2-(1-methylethyl)-4-[3-(piperidin-1-yl)phenyl]-1H-imidazol-1-yl]ethenyl]-4-hydroxy-tetrahydro-2H-pyran-2-one;

(±)-trans-(E)-6-[2-[5-(4-fluorophenyl)-2-(1-methylethyl-4-(3-methylaminomethylphenyl)-1H-imidazol-1-yl]ethenyl]-4-hydroxy-tetrahydro-2H-pyran-2-one;

(±)-trans-(E)-6-[2-[4-(3-(((1,1-dimethylethoxy)carbonyl)amino)phenyl)-5-(4-fluorophenyl)-2-(1-methylethyl)-1H-imidazol-1-yl]ethenyl]-4-hydroxy-tetrahydro-2H-pyran-2-one;

and physiologically acceptable acid addition salts and physiologically acceptable solvates thereof and (±)-erythro-(E)-7-[4-(3-aminophenyl)-5-(4-fluorophenyl)-2-(1-methylethyl)-1H-imidazol-1-yl]-3,5-dihydroxy-6-heptenoic acid;

(±)-erythro-(E)-3,5-dihydroxy-7-[4-(3-dimethylaminophenyl)-5-(4-fluorophenyl)-2-(1-methylethyl)-1H-imidazol-1-yl]-6-heptenoic acid;

(±)-erythro-(E)-3,5-dihydroxy-7-[5-(4-fluorophenyl)-2-(1-methylethyl)-4-[(3-methylthio)phenyl]-1H-imidazol-1-yl]-6-heptenoic acid;

(±)-erthro-(E)-3,5-dihydroxy-7-[5-(4-fluorophenyl)-2-(1-methylethyl)-4-[(3-methylsulphonyl)phenyl]-1H-imidazol-1-yl]-6acid;

(±)-erthro-(E)-7-[4-(3-acetamidophenyl)-5-(4-fluorophenyl)-2-(1-methylethyl)-1H-imidazol-1-yl]-3,5-dihydroxy-6-heptenoic acid;

(±)-erythro-(E)-7-[4-(3-cyclohexylaminophenyl)-5-(4-fluorophenyl)-2-(1-methylethyl)-1H-imidazol-1-yl]-3,5-dihydroxy-6-heptenoic acid;

(±)-erythro-(E)-7-[4-(3-diethylaminophenyl)-5-(4-fluorophenyl)-2-(1-methylethyl)-1H-imidazol-1-yl]-3,5-dihydroxy-6-heptenoic acid;

(±)-erythro-(E)-3,5-dihydroxy-7-[4-(3-(((1,1-dimethylethoxy) carbonyl)amino)phenyl)-5-(4-fluorophenyl)-2-(1-methylethyl)-1H-imidazol-1-yl]-6-heptenoic acid;

(±)-erythro-(E)-3,5-dihydroxy-7-[5-(4-fluorophenyl)-4-[3-(piperidin-1-yl)phenyl]-2-(1-methylethyl)-1H-imidazol-1-yl]-6-heptenoic acid and (±)-erythro-(E)-3,5-dihydroxy-7-[5-(4-fluorophenyl)-4-(3-methylaminomethylphenyl)-2-(1-methylethyl)-1H-imidazol-1-yl]-6-heptenoic acid and physiologically acceptable salts more especially the sodium salts and physiologically acceptable and metabolically labile esters and physiologically acceptable solvates thereof.

Particularly preferred compounds of the invention are (±)-trans-(E)-6-[2-[5-(4-fluorophenyl)-4-(3-methylaminophenyl)-2-(1-methylethyl)-1H-imidazol-1-yl]ethenyl]-4-hydroxy-tetrahydro-2H-pyran-2-one;

and physiologically acceptable acid addition salts and physiologically acceptable solvates thereof and (±)-erythro-(E)-3,5-dihydroxy-7-[5-(4-fluorophenyl)-4-(3-methylaminophenyl)-2-(1-methylethyl)-1H-imidazol-1-yl]-6-heptenoic acid;

and physiologially acceptable salts more especially the sodium salts and physiologically acceptable and metabolically labile esters and physiologically acceptable solvates thereof.

Besides having the utility set forth hereinbefore and hereinafter, every compound of formula (I) is useful as an intermediate in the synthesis of one or more other compounds of formula (I) utilising process (C) described hereinafter.

The compounds of the invention are inhibitors of the enzyme HMG—CoA reductase as demonstrated by their performance in standard in vitro assays known in the art.

Thus, the compounds of the invention inhibit cholesterol biosynthesis and are useful for lowering the level of blood plasma cholesterol in animals, e.g. mammals, especially larger primates, in particular humans, and, therefore the compounds of the invention are useful for the treatment of diseases associated with hypercholesterolemia and hyperlipoproteinemia especially atherosclerosis and coronary heart disease.

There is thus provided as a further aspect of the invention a compound of formula (I) or a physiologically acceptable derivative thereof for use as an active therapeutic agent in particular as a cholesterol-lowering agent, for example in the treatment of diseases associated with hypercholesterolemia and hyperlipoproteinemia.

In a further or alternative aspect there is provided a method for the treatment of a disease associated with hypercholesterolemia and hyperlipoproteinemia in a mammal including man comprising oral administration of an effective amount of a compound of formula (I) or a physiologically acceptable derivative thereof.

In a yet further aspect the invention also provides for the use of a compound of formula (I) or a physiologically acceptable derivative thereof for the manufacture of a medicament for the treatment of a disease associated with hypercholesterolemia and hyperlipoproteinemia.

It will be appreciated by those skilled in the art that reference herein to treatment extends to prophylaxis as well as the treatment of established conditions or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 0.1 to 2000 mg per day e.g. from 1 to 200 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a physiologically acceptable derivative thereof together with one or more physiologically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compounds of the invention may be formulated for administration in any convenient way for use in human or veterinary medicine. Such compositions may be presented for use in a conventional manner with the aid of one or more suitable carriers or excipients. The compositions of the invention include those in a form especially formulated for oral, buccal, parenteral, implant, or rectal administration or in a form suitable for administration by inhalation or insufflation. Oral administration is preferred.

Tablets and capsules for oral administration may contain conventional excipients such as binding agent, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/-sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multidose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Compounds of general formula (I) and salts and solvates thereof may be prepared by the general methods outlined hereinafter. In the following description, the groups $R^1$–$R^5$ and X and Z are as defined for the compounds of general formula (I) unless otherwise stated.

According to a first general process (A) compounds of general formula (I) where Z is a group of formula (a)

and $R^5$ is a hydrogen atom may be prepared by reduction of compounds of formula (II)

(II)

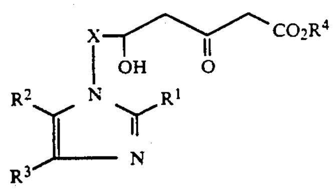

where $R^4$ is as defined in formula (I) above (e.g. a lower alkyl group) with a suitable reducing agent, followed by deprotection where appropriate if a compound of formula (I) in which $R^4$ is a hydrogen atom or a cation is required. Suitable reducing agents include for example metal hydrides such as sodium borohydride.

Reduction with sodium borohydride may optionally be carried out after prior in situ complexation of the compounds of formula (II) with a trialkylborane (e.g. triethylborane or tributylborane) or an alkoxydialkylborane (e.g. methoxydiethylborane).

The reduction conveniently takes place in a protic solvent such as an alcohol (e.g. methanol or ethanol) preferably in the presence of a cosolvent such as an ether (e.g. tetrahydrofuran) at a temperature in the range of −80° to 30° C. (preferably −80° to −40° C.).

Compounds of formula (II) may be prepared by reaction of the aldehydes of formula (III)

(III)

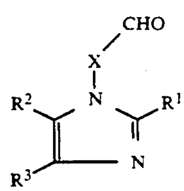

with diketene or a compound of formula (IV)

(IV)

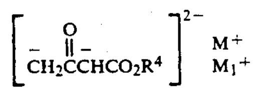

where $M^+$ and $M_1^+$ are metal cations, (e.g. sodium and lithium cations) conveniently prepared in situ from the reaction of

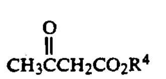

with a base such as a hydride (e.g. sodium hydride) followed by treatment with a strong base such as n-butyllithium or lithium diisopropylamide or alternatively by treatment with two equivalents of a strong base, conveniently in a suitable solvent such as an ether (e.g. tetrahydrofuran) or a hydrocarbon (e.g. hexane) or a mixture thereof at a temperature in the range of −78° C. to room temperature (e.g. −10° to +20° C.).

The reaction with diketene may take place in the presence of a Lewis acid (e.g. titanium tetrachloride) conveniently in a suitable solvent such as a halogenated hydrocarbon (e.g. dichloromethane) at a temperature in the range of −80° to −50° C. followed by subsequent addition of an alcohol $R^4OH$ at a temperature in the range of −30° to −10° C.

Compounds of formula (III) may be prepared by the reduction of a compound of formula (V)

(V)

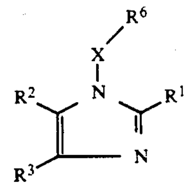

where $R^6$ represents a group CN or a carboxylic ester group.

The reduction may be effected for example using a metal hydride reducing agent such as a dialkylaluminium hydride e.g. diisobutyl aluminium hydride, conveniently in the presence of a solvent such as a halogenated hydrocarbon (e.g. dichloromethane) or an ether (e.g. tetrahydrofuran) at a temperature in the range of −80° to +30° C.

When the group $R^6$ represents a carboxylic ester in the compounds of formula (V), reduction under the above conditions can produce the corresponding alcohols which may be oxidised to the aldehydes of formula (III) using a suitable oxidising agent, for example activated manganese dioxide, pyridinium chlorochromate or pyridinium dichromate in a suitable solvent (e.g. dichloromethane) at ambient temperature.

Compounds of formula (V) may be prepared by reacting the corresponding imidazole of formula (VI) with a compound of formula (VII)

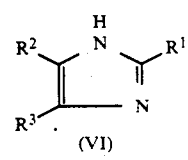

(VI)

$HC{\equiv}C{-}R^6$ (VII)

where $R^6$ as defined in formula (V) above.

The reaction may take place optionally in the presence of a base such as a tertiary amine (e.g. triethylamine) and with or without the presence of a suitable solvent such as an ether (e.g. tetrahydrofuran) at an elevated temperature.

Compounds of formula (III) may also be prepared by reacting the imidazoles of formula (VI) with propiolaldehyde. The reaction may be effected in a suitable solvent such as an ether (e.g. tetrahydrofuran) at an elevated temperature.

When aldehydes of formula (III) are required where X is in the (E) configuration these compounds may conveniently be prepared photochemically from compounds of formula (III) where X is in the (Z) configuration or mixtures of geometric isomers. Thus for example compounds of formula (III) having a mixture of (E) and (Z) isomers (e.g. a 1:1 mixture) may be converted into compounds having the (E) configuration by irradiation with, for example, a tungsten lamp. The reaction may be effected in the presence of a suitable solvent such as a halohydrocarbon (e.g. carbontetrachloride) and in the presence of iodine at an elevated temperature. Compounds of formula (VII) are either known compounds or may be prepared from known compounds using conventional procedures.

It will be appreciated that the imidazoles of formula (VI) are tautomeric with corresponding compounds in which the =N- and -NH- groupings are reversed and that as a consequence, reaction of a compound of formula (VI) with a compound of formula (VII) or propiolaldehyde can give a mixture of products in which the groups $R^2$ and $R^3$ are reversed. Such mixtures, however, may be separated readily for example by chromatography e.g. preparative HPLC at any convenient stage in the reaction scheme.

The imidazoles of formula (VI) may be prepared for example by the reaction of an α-diketone of formula (VIII)

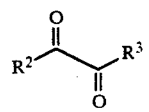

(VIII)

with an aldehyde of formula (IX)

$R^1$—CHO (IX)

or a protected derivative thereof (e.g. a hemiacetal) in the presence of ammonium acetate, conveniently in a suitable solvent such as acetic acid or acetic acid/acetic anhydride conveniently at a temperature in the range of 20°-150° C.

The imidazole intermediates of formula (VI) are novel compounds and thus form a further aspect of the present invention.

It will be appreciated that in some cases it may be more appropriate to prepare imidazoles of formula (VI) where the groups $R^1$, $R^2$ and $R^3$ are in a protected form or represent groups that may be readily converted into the desired groups $R^1$, $R^2$ and $R^3$. This conversion step may take place at any convenient point in the reaction sequence.

One example of the above is the case where compounds are required where $R^1$, $R^2$ or $R^3$ represent phenyl rings substituted by one or more $S(O)_nC_{1-3}$alkyl groups. Such groups may be introduced for example by reacting suitably activated intermediates, for example aryl Grignard reagents or aryl lithium derivatives, with a reagent capable of introducing the group $S(O)_nC_{1-3}$alkyl or a precursor thereof, for example suitable reagents include sulphur, alkyl disulphides or alkyl methanethiolsulphonates.

Alternatively, activation may not be necessary in which case compounds where $R^1$, $R^2$ or $R^3$ represent halosubstituted phenyl rings may be reacted directly with suitable reagents, examples of which include $CuSC_{1-3}$alkyl in the presence of quinoline and pyridine (J. Amer. Chem. Soc., 4927, 81, 1959) or an alkyl thiol in the presence of a phosphonium bromide (J. Org. Chem., 1307 49, 1984).

The above mentioned activated intermediates may be obtained for example from compounds where $R^1$, $R^2$ or $R^3$ represent halo-substituted phenyl rings according to conventional methods, for example, in the case of Grignard reagents, by reaction with metallic magnesium in ethereal solution or, for aryl lithium derivatives, by reaction with a lithiating reagent such as tertbutyl lithium or n-butyl lithium.

For example imidazoles of formula (VI) where one or two of the groups $R^1$, $R^2$ or $R^3$ represent a phenyl ring substituted by a group $S(O)_nC_{1-3}$alkyl where n is zero may be prepared by reacting the corresponding imidazole of formula (VI) where one or two of $R^1$, $R^2$ and $R^3$ represents a halo-(e.g. bromo-) substituted phenyl ring with a lithiating reagent (e.g. n-butyl lithium or tertbutyl lithium) followed by reaction with an alkyl methanethiolsulphonate (e.g. methyl methanethiolsulphonate). The reaction is conveniently carried out in a suitable solvent such as an ether (e.g. tetrahydrofuran) at a temperature in the range of −80° to −40° C.

Prior to the above activation and introduction of the sulphur containing group it may be preferable to protect the protonated nitrogen atom of the imidazoles of formula (VI). Suitable protecting groups are well-known in the art for example an amino acetal derivative may be formed. Examples of such derivatives include substituted ethoxymethyl (e.g., trimethylsilylethoxymethyl) amino derivatives. Such groups may be introduced according to conventional procedures for example by treating the imidazole with a base (e.g. sodium hydride or potassium bis(trimethylsilyl)amide and the corresponding chloromethyl ether (e.g. 2-(trimethylsilyl) ethoxymethyl chloride) in a suitable solvent such as an ether (e.g. tetrahydrofuran). Such groups may be cleaved according to conventional methods for example silyl-substituted ethers may be cleaved using tetrabutylammonium fluoride.

When intermediates are required having phenyl substituents $S(O)_nC_{1-3}$alkyl where n is 1 or 2, these may be prepared from the corresponding intermediates where n is zero according to the methods of process C described hereinafter.

When intermediates are required where the phenyl group substituents represent $(CH_2)_mNR^aR^b$ or $(CH_2)_mNR^cCOR^d$ groups these may be prepared for example by reduction of the corresponding nitro compounds to give the amino compound followed by further elaboration of the amino group where required.

Reduction of the nitro groups may be carried out according to conventional methods for example using hydrogen in the presence of a catalyst (e.g. palladium on carbon) or using a metal hydride reducing agent (e.g. sodium borohydride in the presence of sulphur).

For example imidazoles of formula (VI) where one or two of $R^1$, $R^2$ or $R^3$ represent phenyl rings substituted by an $(CH_2)_mNR^aR^b$ group (or groups) where $R^a$ and $R^b$ both represent hydrogen atoms may be prepared by reduction of the corresponding nitro compounds using a metal hydride such as sodium borohydride in the presence of sulphur. Reduction is conveniently carried out in a suitable solvent such as an ether (e.g. tetrahydrofuran) at a temperature ranging from ambient to the boiling point of the solvent.

In addition, compounds where the phenyl group substituents represent $(CH_2)_r(CH_2)NR^aR^b$ or $(CH_2)_rCH_2NR^cCOR^d$ groups where r is m-1 may be prepared from imidazole intermediates containing suitable aldehyde substituents.

Thus for example compounds where m is 1 may be prepared by reacting the corresponding formyl substituted imidazole with an agent serving to introduce the $NR^aR^b$ or $NR^cCOR^d$ group, such as an alkylamine followed by reduction of the intermediate imine with a suitable reducing agent such as sodium cyanoborohydride. The reaction conveniently takes place in a suitable solvent such as an alcohol (e.g. methanol) at room temperature.

Intermediates where the phenyl substituents represent aldehyde groups may be prepared according to conventional procedures. Thus for example compounds where the phenyl substituents represent formyl groups may be prepared by reacting the corresponding halo-substituted imidazole with a lithiating agent, such as n-butyl lithium, as described above followed by a formylating agent such as dimethylformamide.

Such amino-substituted intermediates may need protection during subsequent reaction steps and suitable amino protecting groups are well-known in the art for example the protecting group may be for example a $C_{7-20}$ aralkyl group (for example a triphenylmethyl or 4-methoxybenzyl group), an acyl group, such as an optionally substituted $C_{1-6}$ alkanoyl group (for example a formyl or chloroacetyl group) or an optionally substituted $C_{1-6}$ alkoxycarbonyl group (for example a tert-butoxycarbonyl or 2,2,2-trichloroethoxycarbonyl group), or a $C_{7-10}$aralkyloxycarbonyl group (for example a benzyloxycarbonyl group) or a silyl group (for example a trimethylsilyl group). Such groups may be introduced according to conventional methods.

For example tertbutoxycarbonyl groups may be introduced using di- tertbutyl dicarbonate in the presence of a base (e.g. sodium carbonate).

As mentioned previously, intermediates where the phenyl substituent(s) represent $(CH_2)_mNR^aR^b$ where $R^a$ and $R^b$ both represent hydrogen atoms may be used to prepare other intermediates where the phenyl substituent(s) represent $(CH_2)_mNR^aR^b$ (where $R^a$ and/or $R^b$ are other than hydrogen) or $(CH_2)_mNR^cCOR^d$ by further elaboration of the amino group, for example using those methods described in process C hereinafter.

When a specific stereoisomer of a compound of formula (I) is required this may be prepared, for example, by resolution of the appropriate enantiomeric mixture of the compounds of formula (I) using conventional methods (see for example "Stereochemistry of Carbon Compounds" by E. L. Eliel (McGraw Hill 1962)).

Thus, where individual enantiomers of the compounds of formula (I) are required, these may be obtained from the enantiomeric mixtures of compounds of formula (I) by chromatography using a chiral column. Alternatively, enantiomeric mixtures of compounds of formula (I) where $R^4$ is an optically active group may be separated for example using fractional crystallisation or chromatography. Enantiomeric mixtures of compounds of formula (I) where $R^4$ is a hydrogen atom or a carboxyl protecting group may be separated by forming an acid additional salt with a suitable chiral acid.

Individual enantiomers of the compounds of formula (I) may also be obtained from the enantiomeric mixtures by selective enzymic hydrolysis.

Thus, a compound where the group $—CO_2R^4$ is a group susceptible to enzymic hydrolysis may be used to obtain one enantiomer of the compound of formula (I) as the free acid and the other enantiomer as the non-hydrolysed compound.

Individual enantiomers of the compounds of formula (I) may also be obtained from intermediates having the required chirality. Such intermediates may be obtained on resolution of their enantiomeric mixtures where the intermediates concerned contain an appropriate chiral centre. For example the intermediates may contain a chiral protecting group. Alternatively, individual enantiomers may be obtained by stereoselective synthesis.

Thus, using general process (A) compounds of general formula (I) where Z is a group of formula (a) and $R^5$ is a hydrogen atom may be prepared having a specific configuration about the 3- and 5-positions for example 3R,5S, in which case the final reduction step would be carried out on a chiral intermediate (IIa):

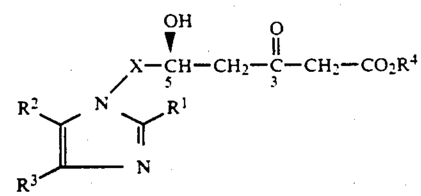
(IIa)

wherein $R^4$ is as defined in formula (I) above (e.g. a lower alkyl group) using a stereoselective reducing agent. Suitable stereoselective reducing agents include for example metal hydrides such as sodium borohydride. Reduction with sodium borohydride may optionally be carried out after prior in situ complexation of the compounds of formula (II) with a trialkylborane (e.g. triethylborane or tributylborane) or an alkoxydialkylborane (e.g. methoxydiethylborane).

The reduction conveniently takes place in a protic solvent such as an alcohol (e.g. methanol or ethanol) preferably in the presence of a cosolvent such as an ether (e.g. tetrahydrofuran) at a temperature in the range of −80° to 30° C. (preferably −80° to −40° C.).

Intermediate enantiomers of formula (IIa) where $R^4$ represents a carboxyl protecting group (e.g. a lower alkyl group) may be prepared by deprotection of a compound of formula (X):

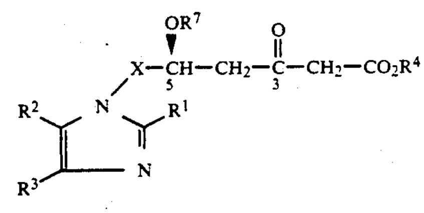
(X)

wherein $R^4$ represents a carboxyl protecting group (e.g. a lower alkyl group) and $R^7$ represents a chiral hydroxyl protecting group for example a chiral optionally substituted alkyl group such as a chiral alkanol (e.g. (R)-3-methylpropan-1-ol).

Deprotection of the hydroxyl group may be effected according to methods known in the art however it will be appreciated that such conditions will be chosen so as not to produce racemization at the C-5 carbon. Thus, for example, when $R^7$ represents a chiral alkanol such as the group

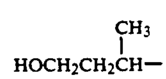
(R)

deprotection may be affected by oxidation to the corresponding aldehyde followed by selective β-elimination.

Suitable oxidising agents for the aforementioned step include periodinanes such as Dess-Martin periodinane (1,1,1-tri(acetyloxy)-1,1-dihydro-1,2-benziodoxol-3(1H)one). Selective β-elimination may take place in the presence of a suitable base for example dibenzylamine or a salt thereof such as the trifluoroacetate salt, conveniently in the presence of a suitable solvent such as a halohydrocarbon (e.g. dichloromethane).

Compounds of formula (X) where $R^7$ represents a group of formula

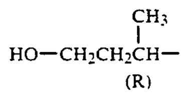

may be prepared by reacting an acetal of formula (XI)

(XI)

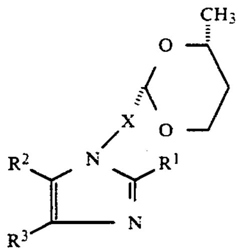

with diketene or a compound of formula (XII)

(XII)

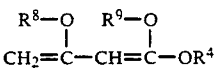

where $R^8$ and $R^9$, which may be the same or different, represent suitable enol stabilising groups and $R^4$ represents a carboxyl protecting group (e.g. a lower alkyl group), followed by removal of the enol stabilising groups.

The aforementioned reaction is highly diastereoselective and conveniently takes place in the presence of a pyridine (e.g. 2,6-di-t-butylpyridine) and a Lewis acid (e.g. titanium tetrachloride) as catalysts in a suitable solvent such as a halogenated hydrocarbon (e.g. dichloromethane) at a temperature in the range of $-70°$ to $-80°$ C. When diketene is employed as a reactant the reaction is followed by subsequent addition of an alcohol $R^4OH$ at a temperature in the range of $-30°$ to $-10°$ C.

Suitable enol stabilising groups represented by $R^8$ and $R^9$ include alkylsilyl groups such as trimethylsilyl groups. Such groups may be removed under conditions of acidic hydrolysis for example using tetrabutylammonium fluoride and acetic acid in a suitable solvent such as an ether (e.g. tetrahydrofuran) conveniently at room temperature. Compounds of formula (XI) may be prepared by reacting a compound of formula (III) with (R)-(−)-butane-1,3-diol in the presence of an acid catalyst such as p-toluenesulphonic acid. The reaction conveniently takes place in the presence of a suitable hydrocarbon solvent (e.g. toluene) at an elevated temperature such as the boiling point of the solvent.

Alternatively the chiral intermediates of formula (IIa) may be prepared by a Claisen condensation of a compound of formula (XIII)

(XIII)

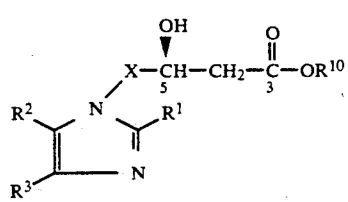

(where $R^{10}$ represents lower alkyl e.g. methyl) with a compound of formula (XIV)

(XIV)

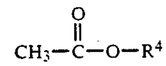

where $R^4$ is a carboxyl protecting group such as a lower alkyl (e.g. t-butyl) group.

The reaction takes place in the presence of a strong base such as a metal amide (e.g. lithium diisopropylamide) conveniently in the presence of a suitable solvent such as an ether (e.g. tetrahydrofuran) or a cycloalkane (e.g. cyclohexane) or mixtures thereof at a temperature in the range of $-40°$ to 5° C.

Compounds of formula (XIII) where $R^{10}$ represents a lower alkyl (e.g. methyl) group may be prepared from compounds of formula (XIII) where $R^{10}$ represents a chiral carboxyl protecting group by transesterification.

Thus compounds of formula (XIII) where $R^{10}$ represents the chiral group

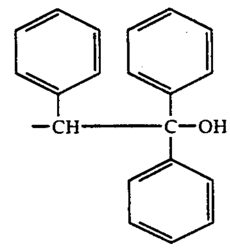

may be reacted with an alkoxide such as an alkali metal alkoxide (e.g. sodium methoxide) in the presence of the appropriate alcohol (e.g. methanol) as solvent.

Compounds of formula (XIII) where $R^{10}$ represents a chiral carboxyl protecting group may be prepared by reacting a compound of formula (III) with an enolate of formula (XV)

(XV)

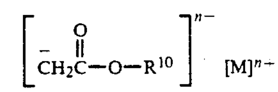

where $R^{10}$ represents a chiral carboxyl protecting group (for example the group

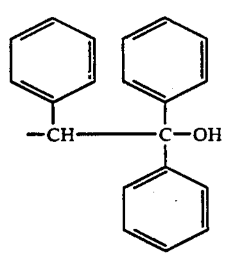

which will thus be in anionic form), M represents a metal (e.g. lithium or magnesium) cation (or cations) and n represents an integer (e.g. 1 or 2) depending on the nature of $R^{10}$ and M, conveniently in a suitable solvent such as an ether (e.g. tetrahydrofuran) at a temperature in the range of $-110°$ to 0° C. The enolate may conveniently be prepared in situ by the treatment of a compound $CH_3C(O)OR^{10}$ with a strong base such as lithium diisopropylamide or lithium dicyclohexylamide (in which case M represents lithium) conveniently in the presence of a suitable solvent such as an ether (e.g. tetrahydrofuran) at a temperature in the range of −80° to 0° C. The enolate thus formed may optionally undergo transmetallation to replace M. Thus for example replacement of M (e.g. by a magnesium cation) may be effected by treatment of a compound of formula (XV) where M represents for example two lithium cations with a metal halide (e.g. magnesium bromide) in the presence of a suitable solvent such as an ether (e.g. tetrahydrofuran) at a temperature in the range of −70° to −80° C.

Compounds of formulae (XII), (XIV) and (XV) are either known compounds or may be prepared according to methods used for the preparation of known compounds.

According to a further general process (B) compounds wherein Z represents a group of formula (a) or (b) and $R^5$ represents a $C_{1-3}$ alkyl group may be prepared by nucleophilic addition of an alkyl acetate anion to a compound of formula (XVI)

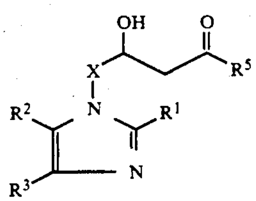

(XVI)

The alkyl acetate anion is conveniently prepared in situ from the action of a base such as a metal amide (e.g. lithium bis(trimethylsilyl)amide) on the corresponding alkyl acetate (e.g. methylacetate).

The reaction conveniently takes place in a suitable solvent such as an ether (e.g. tetrahydrofuran) at a temperature in the range of −80° to −30° C. (e.g. −78° C.).

Compounds of formula (XVI) may be prepared by reacting the aldehydes of formula (III) with a methyl ketone (e.g. acetone) in the presence of a base such as a metal amide (e.g. lithium bis(trimethylsilyl)amide). The reaction conveniently takes place in the presence of a suitable solvent such as an ether (e.g. tetrahydrofuran) at a temperature in the range of −80° to −30° C. (e.g. −78° C.).

Intermediates of formula (II), (III), (V), (X), (XI), (XIII) and (XVI) are novel compounds and therefore form a further feature of the invention.

The novel intermediates of formula (II) have been found to inhibit cholesterol biosynthesis and are therefore useful for the treatment and/or prevention of diseases associated with hypercholesterolemia and hyperlipoproteinemia especially atherosclerosis. Thus the invention also provides a pharmaceutical composition for use in human or veterinary medicine comprising at least one compound of the general formula (II) together with at least one pharmaceutical carrier or excipient.

According to a further general process (C), a compound of formula (I) may be converted into another compound of formula (I) using conventional techniques. Such conventional techniques include protection and deprotection, oxidation, alkylation, reductive alkylation, acylation, lactonisation or base-catalysed cleavage.

Lactonisation according to general process (C) may be used to convert a compound of general formula (I) where Z is a group of formula (a) into a compound of general formula (I) where Z is a group of formula (b) (where (a) and (b) are as defined in formula (I) above).

Thus, compounds of general formula (I) wherein Z is a group of formula (b) may be prepared by lactonization of a compound of formula (I) where Z is a group of formula (a) and $R^4$ is hydrogen or a cation, optionally in the presence of an acid (e.g. p-toluenesulphonic acid) conveniently in a suitable inert solvent such as a hydrocarbon (e.g. toluene) or a halohydrocarbon (e.g. dichloromethane) either at room temperature in the presence of a carbodiimide (e.g. 1-cyclohexyl-3-(2-morpholinoethyl)carbodiimide metho-p-toluenesulphonate) or at an elevated temperature e.g. from 50° C. to the reflux temperature of the solvent.

It will be understood that where racemic compounds of formula (I) where Z is a group (a) are used in the above mentioned lactonization step racemic compounds of formula (I) where Z is a group (b) will be produced. Likewise, where a single enantiomer of a compound of formula (I) is employed in the lactonization step a single enantiomer of formula (I) where Z is a group (b) will be produced. Thus, a racemic erythro compound of formula (I) where Z is a group (a) will give a racemic trans lactone, conversely, a racemic threo compound of formula (I) where Z is a group (a) will give a racemic cis lactone. As a further example a single erythro enantiomer e.g. a 3R,5S enantiomer of a compound of formula (I) where Z represents a group (a) will give a single trans lactone enantiomer e.g. a 4R,6S enantiomer.

Base-catalysed cleavage according to general process (C) may be used to convert a compound of general formula (I) where Z is a group of formula (b) into a compound of general formula (I) where Z is a group of formula (a).

Thus, compounds of general formula (I) wherein Z is a group of formula (a) and $R^4$ is a cation may be prepared by base-catalysed cleavage of compounds of formula (I) where Z is a group of formula (b). Suitable bases include hydroxides such as sodium hydroxide, potassium hydroxide or ammonium hydroxide. Alternatively, compounds of formula (I) wherein Z is a group of formula (a) and $R^4$ represents a carboxyl protecting group such as an ester group, may be prepared by base-catalysed cleavage of compounds of formula (I) where Z is a group of formula (b) in the presence of an alkoxide (e.g. sodium methoxide). The reaction may optionally take place in a solvent such as an ether (e.g. tetrahydrofuran) or an alcohol $R^4OH$ or a mixture thereof, at room temperature.

As mentioned above for the lactonization step, base catalysed cleavage of racemic starting materials will produce racemic products and base catalysed cleavage of single enantiomers will produce products as single enantiomers. Thus, by way of example, base catalysed cleavage of a 4R,6S trans lactone enantiomer will give a compound of formula (I) where Z is a group of formula (a) as a single enantiomer in the 3R,5S erythro configuration.

Oxidation according to general process (C) may be effected for example on a compound of formula (I) wherein n represents zero or 1.

Thus, compounds of formula (I) wherein n is 1 may be prepared for example by treating a compound of formula (I) where n is zero with a suitable oxidising agent.

Compounds of formula (I) wherein n is 2 may be prepared by for example treating a compound of formula (I) where n is zero or 1 with a suitable oxidising agent such as a peracid (e.g. a peroxybenzoic acid such as m-chloroperoxybenzoic acid). The reaction is conveniently carried out in an organic solvent such as a halogenated hydrocarbon (e.g. dichloromethane) at a temperature in the range of −20° to +30° C. (e.g. 0° C.). Alternatively oxidation may be carried out using hydrogen peroxide and selenium(IV)oxide conveniently in a suitable solvent such as an alcohol (e.g. methanol) at ambient temperature.

Alkylation according to general process (C) may be used to convert a compound of general formula (I) where one or more of $R^a$, $R^b$ and $R^c$ represent hydrogen atoms into a compound where one or more of $R^a$, $R^b$ and $R^c$ represent $C_{1-4}$alkyl groups or $R^a$ and/or $R^b$ represent saturated monocyclic 5 to 7 membered rings or $R^a$ and $R^b$ together form a saturated monocyclic 5 to 7 membered ring.

The reaction may be carried out using a suitable alkylating agent such as an alkyl halide (e.g. methyl iodide or 1,5-dibromopentane) or alkylsulphonyloxy group (e.g. trifluoromethanesulphonyloxy, p-toluenesulphonyloxy or methanesulphonyloxy). The alkylation reaction is conveniently carried out in a suitable solvent such as an amide (e.g. dimethylformamide) or acetonitrile at a temperature ranging from 0° C. to the reflux temperature of the solvent optionally in the presence of a base such as an alkali metal hydride (e.g. sodium hydride).

Reductive alkylation according to general process (C) may be used to prepare compounds where one of $R^a$ and $R^b$ represents a hydrogen atom. Thus compounds where $R^a$ and $R^b$ represent hydrogen atoms may be reacted with an appropriate aldehyde or a ketone (e.g. acetaldehyde or acetone) in the presence of molecular sieves followed by a suitable reducing agent such as sodium cyanoborohydride or borane conveniently in a suitable solvent such as an alcohol (e.g. methanol).

Acylation according to general process (C) may be used to convert compounds where one or both of $R^a$ and $R^b$ represent hydrogen atoms into compounds where the amino substituent represents the group $(CH_2)_mNR^cCOR^d$.

Suitable acylating agents include acid anhydrides (e.g. acetic anhydride) for the case where $R^d$ represents a $C_{1-4}$alkyl group or an alkyl pyrocarbonate (e.g. ditert-butyl dicarbonate) for the case where $R^d$ represents a $C_{1-4}$alkoxy group. The reaction conveniently takes place in a suitable solvent and in the presence of a base, for example for the former reaction suitable solvents include halohydrocarbons (e.g. dichloromethane) and ethers (e.g. dioxan) and suitable bases include pyridine and 4N,N-dimethylaminopyridine. In the latter case the reaction may take place under aqueous conditions, with for example sodium carbonate as base. Suitable reaction temperatures range from 0° C. to ambient.

During the above alkylation and acylation reactions it may be necessary to protect any sensitive groups in the molecule for example when Z represents a group of formula (a) it may be necessary to protect the hydroxy groups. Suitable protecting groups are well-known in the art for example the hydroxy groups may be protected by forming an isopropylidene derivative. Such protecting groups may be introduced according to conventional procedures for example using acetone in the presence of zinc chloride. Such groups may be removed for example by acidic hydrolysis e.g. using p-toluenesulphonic acid in methanol.

Deprotection according to general process (C) may be used to convert compounds of formula (I) where the group $R^4$ is a protecting group into compounds of formula (I) where the group $R^4$ is in a deprotected form (i.e. $R^4$ represents a hydrogen atom or a cation).

Deprotection may also be used to convert compounds where $R^d$ represents a $C_{1-4}$alkoxy (e.g. tert-butoxy) group into compounds where the nitrogen substituent represents the group $(CH_2)_mNR^aR^b$ where at least one of $R^a$ and $R^b$ represents a hydrogen atom.

Deprotection may be effected using conventional techniques such as those described in 'Protective Groups in Organic Synthesis' by Theodora W. Green (John Wiley and Sons, 1981). For example tert- butoxycarbonyl groups may be removed under conditions of acidic hydrolysis for example using trifluoroacetic acid in anisole.

The following examples illustrate the invention. Temperatures are in °C. 'Dried' refers to drying using magnesium sulphate. Thin layer chromatography (t.l.c.) was carried out on silica plates. Column chromatography (CC) was carried out on silica (Merck 7734 or 9385). The following solvent systems were used as elutants: System A—ethyl acetate: cyclohexane; System B—ethyl acetate: petroleum ether (40°-60°); System C—ethyl acetate: methanol; System D—chloroform: methanol. The following abbreviations are used: THF—tetrahydrofuran; DMSO—dimethylsulphoxide; ether-diethyl ether.

INTERMEDIATE 1

4(5)-(4-Fluorophenyl)-2-(1-methylethyl)-5(4)-(3-nitrophenyl)-1H-imidazole

To a stirred solution of 1-(4-fluorophenyl)-2-(3-nitrophenyl)-1,2-ethanedione (14.55 g) and anhydrous ammonium acetate (51.10 g) in glacial acetic acid (250 ml) was added isobutyraldehyde (5.28 ml) and the mixture was heated at reflux for 21 h. The mixture was allowed to cool to room temperature and was then added to ice/concentrated aqueous ammonia when a precipitate formed. This mixture was shaken with ethyl acetate (200 ml) when the solid dissolved. The aqueous phase was separated off and extracted with ethyl acetate (2×200 ml). The organic phases were combined, then washed with water (2×200 ml), dried and evaporated to give a red-brown solid (23.2 g). This solid was dissolved in methanol and purified by CC eluting with System A (1:2) to give the title compounds (14.51 g) as a yellow brown crystalline solid. δ(DMSO-$d_6$) values include 1.32(d,J6 Hz, $(CH_3)_2CH$), 3.05(septet,J6 Hz,$(CH_3)_2CH$), 7.16 and 7.32, 7.43–7.53,7.55 and 7.65,7.78 and 7.83,8.01 and 8.13,8.26 and 8.52(t and t,J9 Hz,m,t and t,J≃8 Hz, bd and bd,J≃8 Hz,bd and bd,J≃8 Hz,bs and bs, aromatic protons), 12.22(bs,NH), 12.28(bs,NH).

Similarly prepared:

INTERMEDIATE 2

4(5)-(3-Bromophenyl)-5(4)-(4-fluorophenyl)-2-(1-methylethyl)-1H-imidazole (6.93 g) δ ($CDCl_3$) 1.40 (d, J=7 Hz, $(CH_3)_2CH$) 3.12 (septet, J=7 Hz, $(CH_3)_2CH$), 6.90–7.85 (m, aromatic protons), 9.01 (bs, NH).

From 1-(3-bromophenyl)-2-(4-fluorophenyl)-1,2-ethanedione (6.96 g) and 2-methylpropanal (2.13 g).

INTERMEDIATE 3

4(5)-(3-Bromophenyl)-5(4)-(4-fluorophenyl)-2-(1-methylethyl)-1-[2-(trimethylsilyl)ethoxymethyl]-1H-imidazole 4(5)-(3-Bromophenyl)-5(4)-(4-fluorophenyl)-2-(1-methylethyl)-1H-imidazole (3 g) in dry THF (70 ml) was treated dropwise with a toluene solution of potassium bis(trimethylsilyl)amide (0.5M; 16.7 ml) under nitrogen at −60°. When the addition was complete the mixture was allowed to warm to −40° and was stirred at this temperature, under nitrogen, for 15 min. The solution was then allowed to warm to −20° and 2-(trimethylsilyl)ethoxymethyl chloride (1.39 g) was added dropwise. When the addition was complete the solution was allowed to attain room temperature and stirred under nitrogen for 3 h. Saturated aqueous ammonium chloride solution (50 ml) was added to quench the reaction and the mixture was diluted with water (50 ml) and ethyl acetate (50 ml) and stirred at room temperature for 10 min. The organic phase was separated, dried and evaporated to give a brown oil (4.25 g). This was purified by CC eluting with System A (1:9) to give the title compounds (3.47 g) as a pale yellow-brown oil. νmax ($CHBr_3$) 1506 (aromatic C═C), 1249 ($Me_3Si$), 1249 (C—O), 841 $cm^{-1}$ ($Me_3Si$).

Similarly Prepared:

INTERMEDIATE 4

4(5)-(4-Fluorophenyl)-2-(1-methylethyl)-5(4)-(3-nitrophenyl)-1-(2-(trimethylsilyl)ethoxymethyl)-1H-imidazole (29.12 g) in a (2.5) ratio $R_f$0.51 (System A 1:1) From 4(5)-(4-Fluorophenyl)-2-(1-methylethyl)-5(4)-(3-nitrophenyl)-1H-imidazole (18.33 g) and 2-(trimethylsilyl)ethoxymethyl chloride (11.16 ml).

INTERMEDIATE 5

4-(3-Bromophenyl)-5-(4-fluorophenyl)-2-(1-methylethyl)-1-[2-(trimethylsilyl)ethoxymethyl]-1H-imidazole, (A) and 5-(3-bromophenyl)-4-(4-fluorophenyl)-2-(1-methylethyl)-1-[2-(trimethylsilyl)ethoxy)methyl]-1H-imidazole, (B) From 4-(3-bromophenyl)-5-(4-fluorophenyl)-2-(1-methylethyl)-1H-imidazole (9.3 g) and 2-(trimethylsilyl)ethoxymethyl chloride (4.8 ml). Compound (A) (5.8 g), δ($CDCl_3$) values include 0.04 (s,$(CH_3)_3Si$), 0.86 (t,J9 Hz,$CH_2Si$), 1.48 (d,J6 Hz,$(CH_3)_2CH$), 3.20 (septet,J6 Hz,$CH(CH_3)_2$), 3.36 (t,J9 Hz,$OCH_2CH_2$), 5.05 (s,N—$CH_2O$), 7.04, 7.10–7.40, 7.76 (t,J9 Hz,m,m,aromatic protons). Compound (B) (4.1 g), δ($CDCl_3$) values include 0.03 (s,$(CH_3)_3Si$), 0.89 (t,J9 Hz,$CH_2Si$), 1.45 (d,J6Hz, $(CH_3)_2CH$), 3.18 (septet,J6 Hz, $CH(CH_3)_2$), 3.39 (t, J9 Hz,$OCH_2CH_2$), 5.05 (s,$NCH_2O$), 6.92, 7.15–7.60 (t,J9 Hz,m,aromatic protons).

INTERMEDIATE 6

5(4)-(4-Fluorophenyl)-2-(1-methylethyl)-4(5)-[(3-methylthio)phenyl]-1-[2-(trimethylsilyl)ethoxymethyl]-1H-imidazole 4(5)-(3-Bromophenyl)-5(4)-(4-fluorophenyl)-2-(1-methylethyl)-1-[2-(trimethylsilyl)ethoxymethyl]-1H-imidazole (500 mg) in dry THF (15 ml) was treated dropwise with n-butyl lithium in hexanes (1.6M; 1.28 ml) under nitrogen at −70°. When the addition was complete the solution was stirred under nitrogen at −70° for 15 min. Methyl methanethiolsulphonate (129 mg) was added and the mixture was stirred under nitrogen at −70° for 5 h. The reaction was quenched by the addition of saturated aqueous ammonium chloride (10 ml) and was added to water (100 ml) and extracted with ethyl acetate. The extracts were combined, dried and evaporated to give a pale brown viscous oil (477 mg). This was purified by CC eluting with System B (1:9) to give the title compounds (390 mg) as a pale yellow viscous oil. δ ($CDCl_3$) −0.07 to 0.06 ($Me_3Si$, $CH_2Si$ and reference), 1.44 (d, J=7 Hz, $Me_2CH$), 2.29 and 2.49 (2s, SMe), 3.18 (septet, J=7 Hz, $Me_2CH$) 3.29–2.42 (m, $OCH_2CH_2$), 5.01–5.09 (m, $NCH_2O$), 6.82–7.50 (m, aromatic protons).

INTERMEDIATE 7

5(4)-(4-Fluorophenyl)-2-(1-methylethyl)-4(5)-[(3-methylthio)phenyl]-1H-imidazole 5(4)-(4-Fluorophenyl)-2-(1-methylethyl)-4(5)-[(3-methylthio)phenyl]-1-[2-(trimethylsilyl)ethoxymethyl]-1H-imidazole (2.97 g) in dry THF (40 ml) was treated with a THF solution of tetrabutylammonium fluoride (1M; 8 ml). The solution was heated under reflux for 6 h and then was stood at room temperature for 65 h. A further addition of the tetrabutylammonium fluoride (2 ml) was made and the solution was heated at reflux for 48 h. The solution was evaporated and the residue was partitioned between water (150 ml) and ethyl acetate (2×150 ml). The organic extracts were combined, dried and evaporated to give a brown gum (1.73 g). This was purified by CC eluting with System B (1:1) to give the title compounds (1.055 g) as a colourless solid. δ($CDCl_3$) 1.39 (d, J=7.5 Hz, $Me_2CH$), 2.34 and 2.39 (2s, MeS), 3.14 (septet, J=7.5 Hz, $Me_2CH$), 6.90–7.60 (m, aromatic protons), 8.73 (bs, NH). Similarly prepared:

INTERMEDIATE 8

N-[3-(4(5)-(4-Fluorophenyl)-2-(1-methylethyl)-1H-imidazol-5(4)-yl)phenyl]-N-methylcarbamic acid, 1,1-dimethylethyl ester (34.91 g) as a mixture of tautomers $R_f$ 0.30 (System A 1:1) From N-[3-(4(5)-(4-fluorophenyl)-2-(1-methylethyl)-1-(2-(trimethylsilyl)ethoxymethyl)-1H-imidazol-5(4)-yl)-phenyl]-N-methylcarbamic acid, 1,1-dimethylethyl ester (impure, <0.093 moles) and tetrabutylammonium fluoride (900 ml of a 1.0M solution in THF).

INTERMEDIATE 9

N-[[3-[5-(4-Fluorophenyl)-2-(1-methylethyl)-1H-imidazol-4-yl]phenyl]methyl]methylcarbamic acid, 1,1-dimethylethyl ester (1.1 g) δ($CDCl_3$) values include 1.42 (d, J6 Hz, $(CH_3)_2CH$), 1.46 (s, $CH_3)_3C$), 2.65–2.9 (m, $NCH_3$), 3.15 (septet, J6 Hz, $CH(CH_3)_2$), 6.90–7.60 (m, aromatic protons). From N-[[3-[4-(4-fluorophenyl)-2-(1-methylethyl)-1-(((trimethylsilyl)ethoxy)methyl)-1H-imidazol-5-yl]phenyl]methyl]methylcarbamic acid, 1,1-(dimethyl)ethyl ester (1.8 g) and tetrabutyammonium fluoride (1M in THF; 50 ml).

INTERMEDIATE 10

Methyl (E)-3-[5(4)-(4-fluorophenyl)-2-(1-methylethyl)-4(5)-[(3-methylthio)phenyl]-1H-imidazol-1-yl]-2-propenoate 5(4)-(4-Fluorophenyl)-2-(1-methylethyl)-4(5)-[(3-methylthio)phenyl]-1H-imidazole (1.05 g) in dry THF (50 ml) was treated with methyl propiolate (2.57 g). The solution was heated under reflux, under nitrogen for 19 h when a furthur addition of methyl propiolate (2.57 g) was made. The solution was heated under reflux, under nitrogen for a further 24 h and was then purified by CC eluting with System B (1:5 and 1:3) to give the title compounds (942 mg) as a yellow solid. νmax ($CHBr_3$) 1714 (C═O), 1642 $cm^{-1}$ (C═C). Similarly prepared:

INTERMEDIATE 11

(E) and (Z)-3-[4(5)-(3-(((1,1-Dimethylethoxy)carbonyl)methylamino)phenyl)-5(4)-(4-fluorophenyl)-2-(1-methylethyl)-1H-imidazol-1-yl]-2-propenoic acid, methyl ester (47.81 g); $R_f$ 0.23, 0.29, 0.36 and 0.43 (System A (7:3)). From N-[3-(4(5)-(4-Fluorophenyl)-2-(1-methylethyl)-1H-imidazol-5(4)-yl)-phenyl]-N-methyl carbamic acid, 1,1-dimethylethyl ester (34.83 g) and methyl propiolate (75.4 ml).

INTERMEDIATE 12

(E)-Methyl-3-[4-[3-[((((1,1-(dimethyl)ethoxy)carbonyl)methylamino)methyl)phenyl]]-5-(4-fluorophenyl)-2-(1-methylethyl)-1H-imidazol-1-yl]-2-propenoate (330 mg), δ($CDCl_3$) values include 1.40–1.55 (m, $(CH_3)_2CH$ and $(CH_3)_3C$), 2.60–2.79 (m, $NCH_3$), 3.70 ($COOCH_3$), 4.32 (s, $CH_2N$), 5.29 (d, J15 Hz, CH═CH—$CO_2Me$), 7.00–7.45 (m, aromatic protons), 7.80 (d, J15 Hz, CH═CH—$CO_2Me$). From N-[[3-[5-(4-Fluorophenyl)-2-(1-methylethyl)-1H-imidazol-4-yl]phenyl]methyl]methylcarbamic acid, 1,1-(dimethyl)ethyl ester (1.1 g) and methyl propiolate (2.2 ml).

INTERMEDIATE 13

(E)&(Z)-3-[4(5)-(3-(((1,1-dimethylethoxy)carbonyl)amino)phenyl)-5(4)-(4-fluorophenyl)-2-(1-methylethyl)-1H-imidazol-1-yl]-2-propenoic acid, methyl ester To a solution of N-[3-(4(5)-(4-fluorophenyl)-2-(1-methylethyl)-1H-imidazol-5(4)-yl)-phenyl] carbamic acid, 1,1-dimethylethyl ester (4.77 g) in dry THF (75 ml) was added methyl propiolate (9.90 ml) and the resultant mixture was heated under reflux, under nitrogen, for 66 h. The mixture was allowed to cool to room temperature, concentrated to ca 10–15 ml and then purified by CC eluting with System A (1:4). Early fractions were combined and evaporated to give (E)-3-[4-(3-(((1,1-dimethylethoxy)carbonyl)amino)phenyl)-5-(4-fluorophenyl)-2-(1-methylethyl)-1H-imidazol-1-yl]-2-propenoic acid, methylester (I) (E)-3-[5-(3-(((1,1-dimethylethoxy)carbonyl)amino)phenyl)-4-(4-fluorophenyl)-2-(1-methylethyl)-1H-imidazol-1-yl]-2-propenoic acid, methyl ester (II), as a 55:45 mixture (2.95 g) and as a pale yellow foam. $\nu_{max}$ ($CHBr_3$), 3440(NH), 1719(C═O).

Later fractions were combined and evaporated to give a mixture containing (Z)-3-[5-(3-(((1,1-dimethylethoxy)carbonyl)amino)phenyl)-4-(4-fluorophenyl)-2-(1-methylethyl)-1H-imidazol-1-yl]-2-propenoic acid, methyl ester (III) in addition to (I) and (II), as a 2:9:1 mixture (1.14 g) as a pale yellow foam, $\nu_{max}$ ($CHBr_3$) 3423(NH), 1721(C═O).

Later fractions were combined and evaporated to give a mixture containing (Z)-3-[4-(3-(((1,1-dimethylethoxy)carbonyl)aminophenyl)-5-4-fluorophenyl)-2-(1-methylethyl)-1H-imidazol-2-yl]-2-propenoic cid methyl ester (IV) in addition to (I) and (III), as a 15:12:15 mixture (0.41 g) as a yellow foam, $\nu_{max}$ ($CHBr_3$) 3423(NH), 1723(C═O). fractions were combined and evaporated to give a mixture containing an impure sample of compound (IV) (1.46 g) as a grey/brown foam.

INTERMEDIATE 14

(E)-3-[5(4)-(4-Fluorophenyl)-2-(1-methylethyl)-4(5)-[(3-methylthio)phenyl]-1H-imidazol-1-yl]-2-propenol To a solution of methyl (E)-3-[5(4)-(4-fluorophenyl)-2-(1-methylethyl)-4(5)-[(3-methylthio)phenyl]-1H-imidazol-1-yl]-2-propenoate (934 mg) in dry dichloromethane (30 ml) at −70° under nitrogen was added diisobutyl aluminium hydride (1M solution in dichloromethane, 5 ml). The mixture was stirred at −70° for 2.75 h and was then allowed to attain room temperature. The reaction was quenched by the dropwise addition of saturated aqueous ammonium chloride solution and was added to water (100 ml) with stirring. The mixture was filtered and the filter pad was washed with dichloromethane. The combined washings and filtrate were dried and evaporated to give title compounds (730 mg) as a pale yellow solid. νmax ($CHBr_3$) 3599 (OH), 1670 (C═C), 1506 (aromatic C═C), 1224 (C—O), 1094 (C—O), 841 $cm^{-1}$ (aromatic CH). Similarly prepared:

INTERMEDIATE 15

(E)-3-[4-[3-[((((1,1-(dimethyl)ethoxy)carbonyl)methylamino)methyl)phenyl]]-5-(4-fluorophenyl)-2-(1-methylethyl)-1H-imidazol-1-yl]-2-propenol (320 mg), δ($CDCl_3$) values include 1.42 (d, J6 Hz, $(CH_3)_2CH$), 1.45 (s, $(CH_3)_3C$), 2.60–2.78 (m, N—$CH_3$), 3.18 (septet, J6 Hz, $CH(CH_3)_2$), 4.10–4.21 (m, $CH_2OH$), 4.32 (s, $CH_2N$), 5.52 (m, CH═$CHCH_2OH$), 6.61 (d, J15 Hz, CH═CH—$CH_2OH$), 6.95–7.45 (m, aromatic protons). From (E)-methyl-3-[4-[3-[((((1,1-(dimethyl)ethoxy)carbonyl)methylamino)methyl)phenyl]]-5-(4-fluorophenyl)-2-(1-methylethyl)-1H-imidazol-1-yl]-2-propenoate (330 mg) and diisobutylaluminium hydride (1.5M solution in toluene; 0.95 ml).

INTERMEDIATE 16

(E) & (Z)-N-[3-(4(5)-(4-Fluorophenyl)-1-(3-hydroxy-2-propen-1-yl)-2-(1-methylethyl)-1H-imidazol-5(4)-yl)phenyl]carbamic acid, 1,1-dimethylethyl ester To an impure sample of (E)&(Z)-3-[4(5)-(3-(((1,1-dimethylethoxy)carbonylamino)phenyl)-5(4)-(4-fluorophenyl)-2-(1-methylethyl)-1H-imidazol-1-yl]propenoic acid, methyl ester (5.94 g) in dry dichloromethane (150 ml) at −78° under nitrogen was added diisobutyl aluminium hydride (DIBAL-H) (1M solution in dichloromethane, 15 ml). The mixture was stirred at −78° for 2.5 h and then more DIBAL-H (15 ml) was added. The mixture was stirred at −78° for a further 50 min and was then stirred at 0° for 40 min. Saturated aqueous ammonium chloride solution (100 ml) was added and the resultant two phase mixture was stirred for 18 h and then filtered. The organic layer was separated off, dried, and evaporated to a red brown oil. This material was purified by CC eluting with System A (2:1) to give the title compounds (4.91 g) as a yellow brown foam. $\nu_{max}$($CHBr_3$) 3595(OH), 3425(NH), 1722(C═O).

INTERMEDIATE 17

(E)-3-[(5(4)-(4-Fluorophenyl)-2-(1-methylethyl)-4(5)-[(3-methylthio)phenyl]-1H-imidazol-1-yl]-2-propenal To a stirred solution of (E)-3-[5(4)-(4-fluorophenyl)-2-(1-methylethyl)-4(5)-[(3-methylthio)phenyl]-1H-imidazol-1-yl]-2-propenol (726 mg) in dichloromethane (33 ml) was added manganese (IV) oxide (4.956 g). After 2 h, the reaction mixture was filtered and the spent manganese (IV) oxide was washed with dichloromethane. The combined washings and filtrate were evaporated to give the title compounds (504 mg) as a yellow solid, νmax ($CHBr_3$) 1680 (C═O), 1635 (C═C), 1507 (aromatic C═C), 841 $cm^{-1}$ (aromatic CH). Similarly prepared:

Intermediate 18

(E) and (Z)-N-[3-(4(5)-(4-Fluorophenyl)-1-(3-oxo-2-propen-1-yl)-2-(1-methylethyl)-1H-imidazol-5(4)-yl)phenyl]-N-methylcarbamic acid, 1,1-dimethylethyl ester (9.62 g); $R_f$ 0.44 (System A 1:1) From (E) and (Z)-N-[3-(4(5)-(4-fluorophenyl)-1-(3-hydroxy-2-propen-1-yl)-2-(1-methylethyl)-1H-imidazol-5(4)-yl)phenyl]-N-methylcarbamic acid, 1,1-dimethylethyl ester (11.18 g) and manganese (IV) oxide (82.7 g).

INTERMEDIATE 19

(E)-3-[4-[3-[((((1,1-(Dimethyl)ethoxy)carbonyl)methylamino) methyl)phenyl]]-5-(4-fluorophenyl)-2-(1-methylethyl)-1H-imidazol-1-yl]-2-propenal (230 mg), δ($CDCl_3$) values include 1.40–1.52 (m, $(CH_3)_2CH$ and $(CH_3)_3C$), 2.60–2.78 (m,$NCH_3$), 3.25 (septet,J6 Hz, $CH(CH_3)_2$), 4.35 (s,$CH_2N$), 5.65 (dd,J15 and 6 Hz,CH═CH—CHO), 7.00–7.40 (m,aromatic protons), 7.50 (d,J15 Hz,CH═CHCHO), 9.40 (d,J6 Hz,CHO). From (E)-3-[4-[3-[((((1,1-(Dimethyl)ethoxy)carbonyl)-methylamino) methyl)phenyl]]-5-(4-fluorophenyl)-2-(1-methylethyl)-1H-imidazol-1-yl]-2-propenol (320 mg) and activated manganese dioxide (2.5 g).

INTERMEDIATE 20

N-[3-(4(5)-(4-Fluorophenyl)-2-(1-methylethyl)-1-(3-oxo-2-propen-1-yl)-1H-imidazol-5(4)-yl)phenyl]carbamic acid, 1,1-dimethylethyl ester To a stirred solution of (E) & (Z)-N-[3-(4(5)-(4-fluorophenyl)-1-(3-hydroxy-2-propen-1-yl)-2-(1-methylethyl)-1H-imidazol-5(4)-yl)-phenyl]carbamic acid, 1,1-dimethylethyl ester (4.91 g) in dry dichloromethane (150 ml) was added manganese (IV) oxide (15.65 g). After 3.5 h more manganese (IV) oxide (7.18 g) was added and the mixture was stirred for a further 21 h. The spent manganese (IV) oxide was filtered off and washed with dichloromethane. The filtrate was evaporated to give a yellow brown foam and carbon tetrachloride (70 ml) and iodine (0.037 g) was added. The resultant suspension was heated under reflux in the light of a 200 W tungsten lamp. After 7.5 h the lamp was switched off and the mixture was allowed to cool to room temperature when a precipitate formed. Dichloromethane was added to dissolve the solid and the resultant solution was filtered and then evaporated to a light brown foam. This material was purified by CC eluting with System A (2:5). Early fractions were combined and evaporated to give N-[3-(4-(4-fluorophenyl)-2-(1-methylethyl)-1-(3-oxo-2-propen-1-yl)- 1H-imidazol-5-yl)phenyl]carbamic acid, 1,1-dimethylethyl ester (0.65 g) as a yellow foam. $\nu_{max}$ ($CHBr_3$), 3423(NH), 1725(C═O), 1680(C═O). Later fractions were combined and evaporated to give N-[3-(5-(4-fluorophenyl)-1-(3-oxo-2-propen-1-yl) 2-(1-methylethyl)-1H-imidazol-4-yl)phenyl] carbamic acid, 1,1-dimethylethylester (0.82 g) $\nu_{max}$($CHBr_3$) 3426(NH), 1724(C═O).

Mixed fractions were combined and evaporated to give the title compounds (1.87 g) as a yellow solid.

INTERMEDIATE 21

Methyl (±)-(E)-7-[5(4-fluorophenyl)-2-(1-methylethyl)-4(5)-[(3-methylthio)phenyl]-1H-imidazol-1-yl]-5-hydroxy-3-oxo-6-heptenoate To a slurry of sodium hydride (60% dispersion in oil, 113 mg washed with dry THF (5 ml)), in dry THF (3 ml) at 0° under nitrogen was added methyl acetoacetate (0.14 ml). After 5 min, n-butyl lithium in hexanes (1.6M, 0.82 ml) was added and the resultant solution was stirred at 0° for 10 min. (E)-3-[5(4)-(4-fluorophenyl)-2-(1-methylethyl)-4(5)-[(3-methylthio)phenyl]-1H-imidazol-1-yl]-2-propenal (500 mg) in dry THF (10 ml) was added dropwise into the methyl acetoacetate dianion solution at 0°. After 30 min at 0° the mixture allowed to attain room temperature. The mixture was recooled to 3° and quenched with saturated aqueous ammonium chloride solution (50 ml). This solution was extracted with dichloromethane (3×50 ml) and the extracts were combined, dried and evaporated to give an orange-brown gum (667 mg). This material was purified by CC eluting with System A (2:3) to give the title compounds (299 mg) as a brown gum. δ($CDCl_3$) 1.41 (d, J=7.5 Hz, $Me_2CH$), 2.28 and 2.43 (2 s MeS), 2.56–2.64 (m, $CHCH_2CO$), 3.13 (septet, J=7.5 Hz, $Me_2CH$), 3.44 and 3.46 (2s, $CH_2CO_2Me$), 3.75 (s, $CO_2Me$), 4.57–4.69 (m, CHOH), 5.20–5.32 (m, CH═CHCH), 6.91 and 6.99–7.48 (t, J=9 Hz and m, aromatic protons and NCH═CH). Similarly prepared:

INTERMEDIATE 22a (±)-(E)-7-[5-(3-(((1,1-dimethylethoxy)carbonyl-)amino)phenyl)-4-(4-fluorophenyl)-2-(1-methylethyl)-1H-imidazol-1-yl]-5-hydroxy-3-oxo-6-heptenoic acid, methyl ester (0.071 g) δ($CDCl_3$) 1.51(s,$OC(CH_3)_3$), 2.62–2.86(m,$CH(OH)CH_2C$═O), 3.13(septet,J6 Hz, $(CH_3)_2CH$), 3.50(s,$CH_2CO_2Me$), 3.73(s,$CO_2Me$), 4.62–4.74(m,CHOH), 5.53 (dd,J14 and 6 Hz, CH═CHCH(OH)), 6.67(dd,J14 and 1 Hz,NCH═CH), 6.91 and 6.80–7.60(t,J9 Hz and m, aromatic protons). and INTERMEDIATE 22b (±)-(E)-7-[4-(3-(((1,1-Dimethylethoxy)carbonyl-)amino)phenyl)-5-(4-fluorophenyl)-2-(1-methylethyl)-1H-imidazol-1-yl]-5-hydroxy-3-oxo-6-heptenoic acid, methyl ester (0.068 g) δ($CDCl_3$) values include 1.50(s,$OC(CH_3)_3$), 2.61(d,J6 Hz, $CH(OH)CH_2C$═O), 3.12 (septet,J6 Hz, $(CH_3)_2CH$), 3.45(s,$CH_2CO_2Me$), 3.76(s, $CO_2Me$), 4.58–4.68 (m,CHOH), 5.27(dd, J14 and 6 Hz, NCH═CH), 6.40(bs,NH), 6.70(dd, J14 and 1 Hz, NCH═CH), 7.11 and 6.8–7.6(t,J9 Hz and m, aromatic protons). From N-[3-(4(5)-(4-fluorophenyl)-2-(1-methylethyl)-1-(3-oxo-2-propen-1-yl)-1H-imidazol-5(4)-yl)phenyl]carbamic acid, 1,1-dimethylethyl ester (0.5 g) and methyl acetate (0.14 ml).

INTERMEDIATE 23a (±)-(E)-7-[5-(3-(((1,1-Dimethylethoxy) carbonyl) methylamino)phenyl)-4-(4-fluorophenyl)-2-(1-methylethyl)-1H-imidazol-1-yl]-5-hydroxy-3-oxo-6-heptenoic acid, methyl ester (3.772 g); $R_f$ 0.22 (System A 1:1) and INTERMEDIATE 23b (±)-(E)-7-[5-(3-(((1,1-Dimethylethoxy) carbonyl) methylamino)phenyl)-4-(4-fluorophenyl)-2-(1-methylethyl)-1H-imidazol-1-yl]-5-hydroxy-3-oxo-6-heptenoic acid, methyl ester (3.935 g); $R_f$ 0.15 (System A 1:1) From methyl acetoacetate (12.59 ml) and (E)-N-[3-(4(5)-(4-Fluorophenyl)-1-(3-oxo-2-propen-1-yl)-2-(1-methylethyl)-1H-imidazol-5(4)-yl]-N-methylcarbamic acid, 1,1-dimethylethyl ester (9.012 g)

Intermediate 24

Methyl (±)-(E)-7-[4-[3-[((((1,1-(dimethyl)ethoxy)-carbonyl) methylamino)methyl)phenyl]]-5-(4-fluorophenyl)-2-(1-methylethyl)-1H-imidazol-1-yl]-5-hydroxy-3-oxo-6-heptenoate (0.13 g) δ($CDCl_3$) values include 1.41 (d,J6 Hz, $(CH_3)_2CH$), 1.46 (s, $(CH_3)_3C$), 2.61 (m,$CHOHCH_2CO$), 2.63–2.75 (m,$CH_2N$), 3.12 (septet,J6 Hz,$CH(CH_3)_2$), 3.45 (s,$CH_2CO_2Me$), 3.76 (s,$CO_2CH_3$), 4.35 (s,$CH_2N$), 4.65 (m, CHOH), 5.28 (dd,J15 and 6 Hz,NCH=CH), 6.72, (d,J15 Hz,N—CH—CH), 6.95–7.45 (m, aromatic protons). From methyl acetoacetate (0.24 g) and (E)-3-[4-[3-[((((1,1-(dimethyl)ethoxy)carbonyl)methylamino)methyl)-phenyl]]-5-(4-fluorophenyl)-2-(1-methylethyl)-1H-imidazol-1-yl]-2-propenal (0.2 g).

INTERMEDIATE 25

4(5)-(3-Aminophenyl)-5(4)-(4-fluorophenyl)-2-(1-methylethyl)-1H-imidazole

Dry THF (llml) was added dropwise to a stirred mixture of sodium borohydride (1.59 g) and sulphur (4.05 g). The resulting suspension was stirred for 0.5 h and then a solution of 4(5)-(fluorophenyl)-2-(1-methylethyl)-5(4)-(3-nitrophenyl)-1H-imidazole (4.57 g) in dry THF (80 ml) was added. The mixture was stirred at room temperature for 1 h and then heated under reflux for 1.5 h before being allowed to cool to room temperature. 5% Aqueous sodium hydroxide (200 ml) was added and the resultant mixture was extracted with ethyl acetate (3×100 ml). The organic phases were combined and the product was extracted into 2N hydrochloric acid (2×100 ml). The aqueous layers were combined, washed with ethyl acetate (200 ml) and then basified using 10N aqueous sodium hydroxide. The product was extracted into ethyl acetate (3×100 ml), the extracts were washed with water (100 ml), dried and evaporated to give title compounds (4.08 g) as pale yellow solid. δ(DMSO-$d_6$) values include 1.29(d,J7 Hz,$(CH_3)_2CH$), 2.98(septet, J7 Hz$(CH_3)_2CH$), 4.85–5.35(bs,$ArNH_2$), 6.3–7.7(m, aromatic protons), 11.85(bs,NH). Similarly prepared:

INTERMEDIATE 26

5(4)-(3-Aminophenyl)-4(5)-(4-fluorophenyl)-2-(1-methylethyl)-1-[2-(trimethylsilyl)ethoxymethyl]-1H-imidazole (47.12 g) in a 2:3 ratio, Rf 0.51 and 0.21 (System A 1:1) From 4(5)-(4-fluorophenyl)-2-(1-methylethyl)-5(4)-(3-nitrophenyl)-1-[2-(trimethylsilyl)ethoxymethyl]-1H-imidazole (impure, <0.141 moles) and sodium borohydride (17.16 g) and sulphur (41.40 g).

INTERMEDIATE 27

N-[3-(4(5)-(4-Fluorophenyl)-2-(1-methylethyl)-1H-imidazol-5(4)-yl)-phenyl]carbamic acid, 1,1-dimethylethyl ester Water (50 ml) was added to a stirred solution of 4(5)-(3-aminophenyl-5(4)-(4-fluorophenyl)-2-(1-methylethyl)-1H-imidazole (4.06 g) in 1,4-dioxan (50 ml). To the resultant solution was added di-tertbutyl dicarbonate (3.60 g) followed by anhydrous sodium carbonate (2.92 g). After 21 h the mixture was diluted with water (200 ml) and then extracted with ethyl acetate (3×150 ml). The extracts were combined, dried and purified by CC eluting with System A (3:2) to give a yellow solid. A suspension of this solid in cyclohexane (100 ml) was stirred for 1 h, the solid was filtered-off, washed with cyclohexane and dried in vacuo to give title compounds (4.80 g) as a pale yellow solid. $\nu_{max}$(DMSO) 3440(NH), 1718(C=O). Similarly prepared:

INTERMEDIATE 28

N-[3-(4(5)-(4-Fluorophenyl)-2-(1-methylethyl)-1-[2-(trimethylsilyl) ethoxymethyl]-1H-imidazol-5(4)-yl)-phenyl]carbamic acid, 1,1-dimethylethyl ester (49.03 g) in a 3:7 ratio; Rf 0.35 and 0.21 (System A 1:4) From 5(4)-(3-aminophenyl)-4(5)-(4-fluorophenyl)-2-(1-methylethyl)-1-[2-(trimethylsilyl)ethoxymethyl]-1H-imidazole (impure <0.111 moles) and di-tertbutyl dicarbonate (28.99 g).

INTERMEDIATE 29

N-[[3-[4-(4-Fluorophenyl)-2-(1-methylethyl)-1-[2-(trimethylsilyl) ethoxymethyl]-1H-imidazol-5-yl]phenyl]methyl]methylcarbamic acid,1,1-dimethylethyl ester (1.8 g), δ($CDCl_3$) values include 0.05 (s, $(CH_3)_3Si$), 0.88 (t, J9 Hz, $CH_2Si$), 1.49 (d,J6 Hz, $(CH_3)_2CH$), 1.55 (s,$(CH_3)_3C$), 3.22 (septet,J6 Hz,$CH(CH_3)_2$), 3.38 (t,J9 Hz,$OCH_2CH_2$), 5.10 (s,$NCH_2O$), 6.90, 7.2–7.5 (t,J9 Hz,m, aromatic protons). From 4-(4-Fluorophenyl)-5-[3-(((methyl)amino)methyl)phenyl]-2-(1-methylethyl)-1-[2-(trimethylsilyl)ethoxymethyl]-1H-imidazole (1.5 g) and di-tertbutyl dicarbonate (0.86 g).

INTERMEDIATE 30

6-[2-[(4-(3-Acetamidophenyl)-5-(4-fluorophenyl)-2-(1-methylethyl)-1H-imidazol-1-yl]ethenyl]-5,6-dihydro-2,2-dimethyl-4H-1,3-dioxin-4-acetic acid, methyl ester A solution of zinc chloride (0.43 g) in acetone (4 ml) was heated at reflux for 0.5 h. The mixture was allowed to cool to room temperature and then filtered. A portion of the filtrate (1 ml) was added to (±)-erythro-(E)-7-[4-(3-aminophenyl)-5-(4-fluorophenyl)-2-(1-methylethyl)-1H-imidazol-1-yl]-3,5-dihydroxyheptenoic acid, methyl ester (0.033 g). The resultant solution was heated at reflux, with stirring under nitrogen for 5 h. The reaction mixture was partitioned between saturated aqueous sodium bicarbonate (10 ml) and ethyl acetate (10 ml) and the mixture was stirred overnight. The mixture was filtered and the organic phase was separated off, dried and evaporated to give a yellow brown gum. Acetic anhydride (0.10 ml) was added to a stirred solution of this material (0.030 g), 4-N,N-dimethylaminopyridine (0.009 g) and pyridine (0.21 ml) in dry dichloromethane (1 ml) under nitrogen at 0°. After 3 h at 0° the reaction was quenched with saturated aqueous sodium bicarbonate and the product was extracted into dichloromethane. The organic phase was dried and the solvent was evaporated to give an oily brown gum. To a stirred solution of this material (0.024 g) in methanol (2 ml) was added 1-cyclohexyl-3-(2-morpholinoethyl)carbodiimide metho-p-toluene sulphonate (0.040 g). After 23 h the mixture was purified by preparative t.l.c. eluting with System D (10:1). The appropriate band was removed from the plate and the silica gel was washed with methanol. Evaporation of the solvent gave the title compound (0.005 g) as a yellow gum. δ($CDCl_3$) values include 1.38 and 1.47(s,$(CH_3)_2CO(O)$), 1.41(d,J6 Hz, $(CH_3)_2CH$), 2.13(s,$CH_3CONH$), 2.36 and 2.56(dd,J16 and 7 Hz and dd,J16 and 7 Hz, $CH_2CO_2Me$), 3.71(s,$CO_2Me$), 4.19–4.43(m,$CH(O)CH_2CH(O)CH_2$), 7.09 and 6.90–7.68(t,J9 Hz, and m, aromatic protons).

INTERMEDIATE 31

N-[3-(4(5)-(4-Fluorophenyl)-2-(1-methylethyl)-1-(2-(trimethylsilyl)ethoxymethyl)-1H-imidazol-5(4)-ylphenyl]-N-methylcarbamic acid, 1,1-dimethylethyl ester Sodium hydride (5.59 g of a 60% dispersion in oil) was added over 5 min to a stirred solution of N-[3-(4(5)-(4-fluorophenyl)-2-(1-methylethyl)-1-[2-(trimethylsilyl-)ethoxymethyl]-1H-imidazol-5(4)-yl-phenyl] carbamic acid,1,1-dimethylethyl ester (48.95 g) in dry DMF (460 ml) at 0°. The mixture was stirred at 0° for 0.5 h and at room temperature for 1 h. Methyl iodide (19.87 g) was then added and the solution stirred at room temperature for 3 h. The mixture was then quenched with water and partitioned between water (1700 ml) and ethyl acetate (1700 ml). The phases were separated and the aqueous extracted with ethyl acetate (2×850 ml). The combined organic solutions were dried and evaporated and the residue purified by suction flash CC eluting with System A ((0:1), (1:19), (3:17), (1:4)) to give an impure sample of the title compounds (53:36 g) in a (2:1) ratio as a brown/orange gum. $R_f$0.19 and 0.28 (System A 1:4).

INTERMEDIATE 32

(E) and (Z)-N-[3-(4(5)-(4-Fluorophenyl)-1-(3-hydroxy-2-propen-1-yl)-2-(1-methylethyl)-1H-imidazol-5(4)-yl)phenyl]-N-methylcarbamic acid,1,1-dimethylethyl ester To a solution of (E) and (Z)-3-[4(5)-(3-(((1,1-dimethylethoxy)carbonyl)-methylamino)phenyl-5(4)-(4-fluorophenyl)-2-(1-methylethyl)-1H-imidazol-1-yl]-2-propenoic acid, methyl ester (48.2 g) in dry dichloromethane (800 ml) at −78° under nitrogen was added diisobutyl aluminium hydride (1M solution in dichloromethane, 215 ml). The mixture was stirred at −78° for 0.75 h and allowed to attain room temperature over 0.5 h. The mixture was then recooled to −78° and a further addition of diisobutyl aluminium hydride (1M solution in dichloromethane, 86 ml) was made. The solution was allowed to reach room temperature over 1h, recooled to −78° and more diisobutyl aluminium hydride (1M solution in dichloromethane, 30 ml) was added. The solution was allowed to reach room temperature over 0.5 h then the reaction quenched by the dropwise addition of saturated aqueous ammonium chloride solution (600 ml) over 1 h. Dichloromethane (500 ml) was added, the slurry filtered and the filter pad washed with dichloromethane (1000 ml) and ethyl acetate (1000 ml). The washings and filtrate were combined, the organic phase separated, dried and evaporated to an orange gum. This was then purified by CC eluting with System A ((3:7), (1:1)) to give one pure sample of the title compounds and an impure orange gum. The latter was further purified by CC eluting with System A ((3:7), (1:1)) and all appropriate fractions combined with the previous pure sample to give the title compounds (30.13 g) as a yellow/orange foam. $R_f$ 0.21 and 0.26 (System A 1:1).

INTERMEDIATE 33

(E)-N-[3-(4(5)-(4-Fluorophenyl)-1-(3-oxo-2-propen-1-yl)-2-(1-methylethyl)-1H-imidazol-5(4)-yl)phenyl]-N-methyl carbamic acid,1,1-dimethylethyl ester A solution of (E) and (Z)-[3-(4(5)-(4-fluorophenyl)-1-(3-oxo-2-propen-1-yl)-2-(1-methylethyl)-1H-imidazol-5(4-yl)phenyl]-N-methyl carbamic acid,1,1-dimethylethyl ester (9.62 g) and iodine (0.067 g) in carbon tetrachloride (170 ml) was heated under reflux in the light of a 200 W tungsten lamp. After 20 h the lamp was switched off, the solution allowed to cool to room temperature and then evaporated to give a brown gum. This was dissolved in ethyl acetate (500 ml) and washed with aqueous sodium sulphite solution (300 ml), water (300 ml), then dried, evaporated and purified by CC eluting with System A (1:2) to give the title compounds (17.53 g) as an orange foam. $R_f$0.46 (System A 1:1).

INTERMEDIATE 34

3-[4-(4-Fluorophenyl)-2-(1-methylethyl)-1-[((trimethylsilyl) ethoxy)methyl]-1H-imidazol-5-yl]benzenecarboxaldehyde To a solution of 5-(3-Bromophenyl)-4-(4-fluorophenyl)-2-(1-methylethyl)-1-[((trimethylsilyl)ethoxy)methyl]-1H-imidazole (4.4 g) in dry THF (50 ml) at −50° under $N_2$ was added n-butyllithium (1.6M, 8.4 ml). After 15 min at −50° the mixture was treated with dimethylformamide (0.7 ml) and stirred at this temperature for 1.5 h. It was then quenched with water (50 ml) and brine (50 ml) and extracted with ethyl acetate (100 ml). The extracts were dried and evaporated to give a crude product which was purified by CC with System B (1:3) to give the title compound (2.9 g) δ($CDCl_3$) values include 0.05 (s, $(CH_3)_3Si$), 0.90 (t, 9 Hz, $CH_2Si$), 1.49 (d, J6 Hz, $(CH_3)_2CH$, 3.23 (septet,J6 Hz, $CH(CH_3)_2$), 3.40 (t,9 Hz, $OCH_2CH_2$), 5.08 (s, $NCH_2O$), 6.92, 7.42, 7.58–7.68, 7.95–8.00 (t,J9 Hz,m,m,m,aromatic protons), 10.05 (CHO).

INTERMEDIATE 35

4-(4-Fluorophenyl)-5-[3-((methylamino)methyl-phenyl]-2-(1-methylethyl)-1-[2-(trimethylsilyl)ethoxymethyl]-1H-imidazole To a solution of 3-[4-(4-fluorophenyl)-2-(1-methylethyl)-1-[2-(trimethylsilyl)ethoxymethyl]-1H-imidazol-5-yl] benzenecarboxaldehyde (440 mg) in methanol (2.5 ml) at 20° was added methylamine hydrochloride (dried in vacuo at 50°; 609 mg) and methylamine (33% w/w ethanolic solution; 0.8 ml). After stirring at 20° for 15 min sodium cyanoborohydride (38 mg) was added and the mixture was stirred at 20° for 72 h then diluted with water (5 ml) and basified with excess sodium bicarbonate. Extraction with ethyl acetate afforded the crude product which was purified by CC eluting with light petroleum, ethyl acetate and methanol (10:10:3) to give the title compound (220 mg), δ($CDCl_3$) values include 0.03 (s,$(CH_3)_3Si$), 0.87 (t, 9 Hz,$CH_2Si$), 1.49 (d, J6 Hz,$(CH_3)_2CH$, 3.23 (septet,J6 Hz,$CH(CH_3)_2$), 3.27 (t,J9 Hz, $OCH_2CH_2$), 5.10 (s,$NCH_2O$), 6.91, 7.22–7.60 (t,J9 Hz,m,aromatic protons).

EXAMPLE 1

Methyl (±)-erythro-(E)-3,5-dihydroxy-7-[4-(4-fluorophenyl)-2-(1-methylethyl)-5-[(3-methylthio)-phenyl]-1H-imidazol-1-yl]-6-heptenoate To a solution of triethylborane (1M solution in THF, 0.82 ml) in dry THF (2 ml) at room temperature under nitrogen was added dry methanol (1.53 ml) and the resulting mixture was stirred for 30 min at room temperature and then cooled to −70°. Methyl (±)-(E)-7-[5(4)-(4-fluorophenyl)-2-(1-methylethyl)-4(5)-[(3-methylthio)phenyl]-1H-imidazol-1-yl]-5-hydroxy-3-oxo-6-heptenoate (290 mg) in THF (20 ml) was added and the mixture was stirred for 1.5 h. Sodium borohydride (27 mg) was added and after stirring at −70° for 5 h, the reaction was quenched with saturated aqueous ammonium chloride solution (20 ml). The resultant mixture was allowed to attain room temperature and was diluted with water (100 ml) and extracted with ethyl acetate (2×100 ml). The organic extracts were combined, dried and evaporated to give an orange gum. This material was azeotroped four times with methanol (50 ml) to give a yellow foam (261 mg). This was purified by CC eluting with System A (2:3) to give a pale yellow gum (220 mg). A portion (94 mg) of this material was subjected to preparative h.p.l.c. (Zorbax $NH_2$ column) eluting with 40% (75:20:5 cyclohexane:dichloromethane:methanol): 60% (80:20 cyclohexanedichloromethane). Appropriate fractions which contained the less polar component were combined and evaporated to give the title compound (17 mg) as a colourless film. Rf 0.43 (System B 1:3), δ($CDCl_3$) 1.39 (d, J=7.5 Hz, $Me_2CH$), ca.1.4–1.6 (m, $CH(OH)CH_2CH(OH)$), 2.41 (s, MeS), 2.46 (d, J=6 Hz, $CH_2CO_2Me$), 3.15 (septet, J=7.5 Hz, $Me_2CH$), 3.73 (s, $CO_2Me$), 4.09–4.23 (m, $CH_2CH(OH)CH_2CO_2Me$), 4.38–4.50 (m, CH=CHCH), 5.31 (dd, J=14 Hz, 5 Hz, CH=CHCH), 6.69 (d, J=14 Hz, NCH=CH), 6.90, 7.03, 7.11, 7.17–7.33 and 7.44 (t, J=9 Hz, d, J=7.5 Hz, s, m, dd, J=3.5 Hz, 8.75 Hz, aromatic protons).

Appropriate fractions which contained the more polar component were combined and evaporated to give:

EXAMPLE 2

Methyl (±)-erythro-(E)-3,5-dihydroxy-7-[5-(4-fluorophenyl)-2-(1-methylethyl)-4-[(3-methylthio)-phenyl]-1H-imidazol-1-yl]-6-heptenoate (23 mg) as a colourless opaque solid. Rf 0.38 (System B) (1:3); δ($CDCl_3$) 1.41 (d, J=7 Hz, $Me_2CH$), ca.1.23–ca.1.6 (m, $CH(OH)CH_2CH(OH)$), 2.28 (s, MeS), 2.45 (d, J=6 Hz, $CH_2CO_2Me$), 3.15 (septet, J=7 Hz, $Me_2CH$), 3.74 (s, $CO_2Me$), 4.09–4.24 (m, $CH_2CH(OH)CH_2CO_2Me$), 5.31(dd, J=14 Hz, 5 Hz, CH=CH.CH), 6.68 (d,J=14 Hz, NCH=CH), 4.37–4.49 (m, CH=CH.CH), 7.0–7.48 (m, aromatic protons).

EXAMPLE 3

Methyl (±)-erythro-(E)-3,5-dihydroxy-7-[5(4)-(4-fluorophenyl)-2-(1-methylethyl)-4(5)-[(3-methylsulphonyl)phenyl]-1H-imidazol-1yl]-6-heptenoate To a solution of methyl (±)-erythro-(E)-3,5-dihydroxy-7-[5(4)-4-fluorophenyl)-2-(1methylethyl)-4(5)-[(3-methylthio)phenyl]-1H-imidazol-1-yl]-6-heptenoate (86 mg) in dichloromethane (17 ml) at 0° was added m-chloroperoxybenzoic acid (50–55%, 66 mg). The mixture was stirred at 0° for 2 h when a further addition of m-chloroperoxybenzoic acid (13 mg) was made. After a further 1 h at 0° another addition of m-chloroperoxybenzoic acid (15 mg) was made and the mixture stirred at 0° for 2 h. The mixture was purified by CC (Merck Kieselgel 60) eluting with System A (2:1→1:0) and finally with System C (9:1) to give title compounds (36 mg) as a pale yellow gum, δ($CDCl_3$), 1.38 (d, J=7 Hz, $Me_2CH$), ca. 1.4–1.70 (m, $CH(OH)CH_2CH(OH)$), 2.40–2.55 (m, $CH(OH)CH_2CO_2Me$), 2.99 and 3.08 (2s, $MeSO_2$), ca. 2.9–3.25 (septet, J=7 Hz, $Me_2CH$), 3.70 (s, $CO_2Me$), ca. 4.05–4.30 (m, $CH(OH)CH_2CO_2Me$), 4.38–4.55 (m, CH=CH.CH(OH)) 5.28–5.50 (m, CH=CHCH(OH)), 6.69 (d, J=15 Hz, CH=CHCH(OH)), 6.95 and 7.04–8.15 (t, J=9 Hz and m, aromatic protons).

EXAMPLE 4

Methyl (±)-erythro-(E)-3,5-dihydroxy-7-[4-(4-fluorophenyl)-2-(1-methylethyl)-5-[(3-methylsulphonyl)phenyl]-1H-imidazol-lyl]-6-heptenoate To a solution of methyl (±)-erythro-(E)-3,5-dihydroxy-7-(5(4)(4-fluorophenyl)-2-(1-methylethyl)-4(5)-[(3-methylthio)phenyl]-1H-imidazol-1-yl]-6-heptenoate (40 mg) in methanol (7ml) was added selenium (IV) oxide (9 mg) and 30% hydrogen peroxide solution (0.05 ml). The mixture was stirred at room temperature and after 2 and 4 h further additions of 30% hydrogen peroxide solution (0.1 ml) were made. The mixture was stirred at room temperature for 18 h and was then evaporated. The residue was purified by CC eluting with System C (19:1) to give a pale yellow gum (45 mg). This was combined with the product of Example 3 (36 mg) and subjected to preparative h.p.l.c. (Zorbax $NH_2$ column) eluting with 80% (cyclohexane:dichloromethane:methanol (75:20:5)): 20% (cyclohexane:dichloromethane (80:20)). Appropriate fractions which contained the less polar component were combined and evaporated to give the title compound (17 mg) as a colourless foam. Rf 0.29 (ethyl acetate); δ($CDCl_3$) 1.41 (d, J=6 Hz, $Me_2CH$), ca. 1.47–1.70 (m, $CH(OH)CH_2CH(OH)$), 2.49 (d, J=6 Hz $CH_2CO_2Me$), 3.07 (s, $MeSO_2$), 3.15 (septet, J=6 $H_2$, $Me_2CH$), 3.71 (s, $CO_2Me$), 4.15–4.30 (m, $CH_2CH(OH)CH_2CO_2Me$), 4.43–4.54 (m, CH=CH.CH), 5.41 (dd, J=14 Hz, J=6 Hz, CH=CH.CH), 6.68 (d, J=14 Hz, NCH=CH), 7.40, 6.93 and 7.51–7.92 (dd, J=9 Hz, J=5 Hz, t, J=9 Hz and m, aromatic protons).

Appropriate fractions which contained the more polar component were combined and evaporated to give:

EXAMPLE 5

Methyl (±)-erythro-(E)-3,5-dihydroxy-7-[5-(4-fluorophenyl)-2-(1-methylethyl)-4-[(3-methylsulphonyl)phenyl]-1H-imidazol-1-yl]-6-heptenoate (29 mg) as a colourless solid. Rf 0.23 (ethyl acetate); δ($CDCl_3$) 1.41 (d, J=7 Hz, $Me_2CH$), ca.1.45–ca.1.70 (m, $CH(OH)CH_2CH(OH)$), 2.46 (d, J=7 Hz, $CH_2CO_2Me$), 2.97 (s, $MeSO_2$), 3.15 (septet, J=7 Hz, $Me_2CH$), 3.74 (s, $CO_2Me$), 4.09–4.24 (m, $CH_2CH(OH)CH_2CO_2Me$), 4.39–4.50 (m, CH=CH.CH), 5.35 (dd, J=14 Hz, 5 Hz, CH=CH.CH), 6.69 (d, J=14 Hz, NCH=CH), 7.12, 7.21–7.30, 7.36, 7.61, 7.71 and 8.10 (t, J=9 Hz, m, t, J=7 Hz, d, J=7 Hz, and s, aromatic protons).

EXAMPLE 6

(±)-Erythro-(E)-7-[4-(3-aminophenyl)-5-(4-fluorophenyl)-2-(1-methylethyl)-1H-imidazol-1-yl]-3,5-dihydroxy-6-heptenoic acid, methyl ester To a solution of (±)-erythro-(E)-3,5-dihydroxy-7-[4-(3-(((1-dimethylethoxy)carbonyl)amino)phenyl)-5-(4-fluorophenyl)-2-(1-methylethyl)-1H-imidazol-1-yl]-6-heptenoic acid, methyl ester (0.060 g) in anisole (1 ml) at 3° was added trifluoroacetic acid (4 ml) at 3° and the resultant red/brown solution was stirred at 3° for 0.75 h. Ethyl acetate (10 ml) was added and the mixture was basified with saturated aqueous sodium bicarbonate whilst cooling. The aqueous phase was separated off and extracted with ethyl acetate (2×10 ml). The organic solutions were combined, dried and evaporated to give a red/brown oil. This material was purified by preparative t.l.c. eluting with System C (20:1). The appropriate band was removed and the silica gel washed with System C (8:1). The solvent was evaporated to give the title compound (0.042 g) as a brown gum, $R_f$0.46 (ethylacetate), δ(DMSO-$d_6$) values include 1.29(d, J7 Hz, $(CH_3)_2CH$), 2.26 and 2.39 (dd,J15 and 8 Hz,dd,J15 and 5 Hz,$CH_2CO_2Me$), 3.17 (septet,J7 Hz,$(CH_3)_2CH$), 3.59 (s, $CO_2Me$), 3.68–3.82(m,$CH(OH)CH_2CO_2Me$), 4.09–4.23 (m,CH=CHCH(OH)), 5.42 (dd, J14 and 5 Hz, NCH=CH), 6.59 (d,J14 Hz, NCH=CH), 6.29, 6.34, 6.77, 6.86, 7.24 and 7.17–7.38

(bd,J9 Hz,bd,J9 Hz,t,J8 Hz, bs,t,J9 Hz and m, aromatic protons). Similarly prepared:

EXAMPLE 7

(±)-Erythro-(E)-7-[5-(3-aminophenyl)-4-(4-fluorophenyl)-2-(1-methylethyl-1H-imidazol-1-yl]-3,5-dihydroxy-6-heptenoic acid, methyl ester (0.020 g) as a hard light brown gum. $R_f$ 0.52 (ethylacetate-ethanol (15:1)), δ($CDCl_3$ and $CD_3OD$) values include 1.42(d,J6 Hz,$(CH_3)_2CH$), 2.49(d, J6 Hz,$CH_2CO_2Me$), 3.22(septet,J6 Hz,$(CH_3)_2CH$), 3.73(s,$CO_2Me$), 5.49(dd, J14 and 7 Hz,NCH=CH), 6.91,7.15 and 6.60–7.50(t,J9 Hz,t,J8 Hz and m, aromatic protons). From (±)-erythro-(E)-3,5-dihydroxy-7-[5-(3-(((1, 1-1-dimethylethoxy)carbonyl)amino)phenyl)-4-(4-fluorophenyl)-2-(1-methylethyl)-1H-imidazol-1-yl]-6-heptenoic acid, methyl ester (0.030 g).

EXAMPLE 8

Methyl (±)-erythro-(E)-3,5-dihydroxy-7-[5-(4-fluorophenyl)-4-[3-((methylamino)methyl)phenyl]-2-(1-methylethyl)-1H-imidazol-1-yl]-6-heptenoate (25 mg), δ($CDCl_3$) values include 1.40 (d,J6 Hz, $(CH_3)_2CH$), 2.45 (s,$CH_3N$), 3.12 (septet,J6 Hz, $CH(CH_3)_2$), 3.75 (s,$CO_2CH_3$), 3.85 (s,$CH_2N$), 4.42 (m,CHOH), 5.28 (dd,J15 and 6 Hz,NCH=CH), 5.63 (d,J15 Hz,NCH=CH), 7.00–7.42 (m,aromatic protons). From methyl (±)-(E)-erythro-3,5-dihydroxy-7-[4-[3-[((((1,1-(dimethyl)ethoxy)carbonyl)methylamino)methyl)-phenyl]]-5-(4-fluorophenyl)-2-(1-methylethyl)-1H-imidazol-1-yl]-6-heptenoate (120 mg) anisole (1 ml) and trifluoroacetic acid (4 ml).

EXAMPLE 9

(±)-Erythro-(E)-3,5-dihydroxy-7-[4-(3-dimethylaminophenyl)-5-(4-fluorophenyl)-2-(1-methylethyl)-1H-imidazol-1-yl]-6-heptenoic acid, methyl ester To a stirred solution of (±)-erythro-(E)-7-[4-(3-aminophenyl)-5-(4-fluorophenyl)-2-(1-methylethyl)-1H-imidazol-1-yl]-3,5-dihydroxy-6-heptenoic acid, methyl ester (0.050 g) in acetonitrile (1 ml) was added methyl iodide (0.003 ml) and the resultant solution was heated to reflux under nitrogen for 3 h. The reaction mixture was allowed to cool to room temperature and then evaporated to dryness. The residue was purified by CC eluting with System D (10:1). Early fractions were combined and evaporated to give a yellow gum (0.009 g). Later fractions were combined and evaporated to give impure starting material. This latter material in acetonitrile (1 ml) was treated with methyl iodide (0.005 ml) and the resultant mixture was heated at reflux under nitrogen for 2 h before evaporating and purifying as described above. Early fractions were combined and evaporated to give a yellow gum (0.024 g). This material was combined with material from the previous column (0.009 g) and also material (0.010 g) from a previous reaction. This material was separated using HPLC (Zorbax $NH_2$ column) eluting isocratically with 70% (cyclohexane-dichloromethane-methanol (75:20:5))-30% (cyclohexane-dichloromethane (80:20)). Early fractions were combined and evaporated to give the title compound (0.006 g) as a pale yellow oil. $R_f$0.54 (ethyl acetate), δ($CDCl_3$) values include 1.42(d,J7 Hz, $(CH_3)_2CH$), 2.47(d,J6 Hz,$CH_2CO_2Me$), 2.78(s,$N(CH_3)_2$), 3.16(septet,J6 Hz, $(CH_3)_2CH$), 3.75(s,$CO_2Me$), 4.09–4.22(m, $CH(OH)CH_2CO_2Me$), 4.37–4.49 (m,CH=CHCH(OH)), 5.31(dd,J=14 and 6 Hz, NCH=CH), 6.68(dd,J14 and 1 Hz, NCH=CH), 6.56,6.79,6.85, 7.07,7.09 and 7.22–7.33(dd, J8 and 2 Hz,bs,bd,J8 Hz,t,J9 Hz, t,J8 Hz and m, aromatic protons). Later fractions were combined and evaporated to give:

EXAMPLE 10

(±)-Erythro-(E)-3,5-dihydroxy-7-[5-(4-fluorophenyl)-4-(3-methylaminophenyl)-2-(1-methylethyl)-1H-imidazol-1-yl]-6-heptenoic acid, methyl ester (0.011 g) as a pale yellow film. $R_f$ 0.55 (System D (10:1)) δ($CDCl_3$) values include 1.42 (d,J7 Hz,$(CH_3)_2CH$), 2.45(d,J6 Hz,$CH_2CO_2Me$), 2.71(s,$NCH_3$), 3.15(septet, J7 Hz, $(CH_3)CH$)), 3.74(s,$CO_2Me$), 4.09–4.22(m,$CH(OH)CH_2CO_2Me$), 4.36–4.49(m,CH=CHCH(OH)), 5.31(dd,J14 and 6 Hz,NCH=CH), 6.67(d,J14 Hz, NCH=CH), 6.43,6.67–6.81,7.01,7.07,7.20–7.34(dd,J8 and 2 Hz, m,t,J8 Hz, t, J9 Hz,m, aromatic protons). This sample contained 10% of an impurity.

EXAMPLE 11

(±)-Erythro-(E)-7-[4-(3-acetamidophenyl)-5-(4-fluorophenyl)-2-(1-methylethyl)-1H-imidazol-1-yl]-3,5-dihydroxy-6-heptenoic acid, methyl ester To a solution of 6-[2-[(4-(3-acetamidophenyl)-5(4-fluorophenyl)-2-(1-methylethyl)-1H-imidazol-1-yl]ethenyl]-5,6-dihydro-2,2-dimethyl-4H-1,3-dioxin-4-acetic acid, methyl ester (0.005 g) in dry methanol (0.5 ml) was added p-toluenesulphonic acid monohydrate (PTSA) (0.001 g). The resultant solution was kept at room temperature for 16 h and at −22° for a total of 69 h before more PTSA (0.001 g) was added. After a further 2 h at room temperature the mixture was purified by preparative t.l.c. eluting with System D (10:1). The silica gel was washed with System D (10:0.5) and the solvent was evaporated to give the title compound (0.003 g) as an off white, tacky solid. $R_f$0.27 (System D 10:1), δ($CDCl_3$) values include 1.41(d,J6 Hz,$(CH_3)_2CH$), 2.14 (s,$CH_3CONH$), 2.45(d,J6 Hz,$CH_2CO_2Me$), 3.14(septet,J6 Hz,$(CH_3)_2CH$), 3.74(s,$CO_2Me$), 4.10–4.23(m,$CHCH_2CO_2Me$), 4.38–4.48(m,CH=CHCH(OH)), 5.31(dd,J15 and 5 Hz,NCH=CH), 6.66(dd, J15 and 1 Hz,NCH=CH), 7.09 and 6.90–7.68(t,J9 Hz and m, aromatic protons)

EXAMPLE 12

(±)-Erythro-(E)-3,5-dihydroxy-7-[5-(3-(((1,1-dimethylethoxy)carbonyl)amino)phenyl)-4-(4-fluorophenyl)-2-(1-methylethyl)-1H-imidazol-1-yl]6-heptenoic acid, methyl ester A solution of triethyl borane (1M solution in THF, 0.23 ml) was added to a mixture of dry THF (2.3 ml) and anhydrous methanol (0.42 ml) at room temperature under nitrogen. After stirring for 1 h the mixture was cooled to −78° followed by the addition of (±)-(E)-7-[5-(3-((1,1-dimethylethoxy)carbonyl)amino)phenyl)-4-(4-fluorophenyl)-2-(1-methylethyl)-1H-imidazol-1-yl]-5-hydroxy-3-oxo-6-heptenoic acid, methyl ester (0.065 g) in dry THF (1 ml) at −78°. Stirring was continued for 0.75 h and then sodium borohydride (0.009 g) was added. The mixture was stirred at −78° for 2.5 h and then quenched with saturated aqueous ammonium chloride. The mixture was extracted with ethyl acetate, the extracts were combined, dried and evaporated. The residue was evaporated from methanol (3×15 ml) to give the title compound (0.062 g) as a brown gum. δ($CDCl_3$) values include 1.40 and 1.42(d,J6 Hz and d,J6 Hz,$(CH_3)_2)CH$), 1.50(s,$OC(CH_3)_3$), 2.39–2.60 (m, $CH_2CO_2Me$), 3.14 and 3.15(septet J6 Hz,$(CH_3)_2CH$), 3.72(s, $CO_2Me$), 4.12–4.35(m,$CH(OH)CH_2CO_2Me$), 4.43–4.57(m,CH=CHCH(OH)), 5.58 (dd,J14 and 7 Hz,NCH=CH), 6.62(d,J14 Hz, NCH=CH), 6.91 and 6.82–7.62(t,J9 Hz and m, aromatic protons). Similarly prepared:

EXAMPLE 13

(±)-Erythro-(E)-3,5-dihydroxy-7-[4-(3-(((1,1-dimethylethoxy)carbonylamino)phenyl)-5-(4-fluorophenyl)-2-(1-methylethyl)-1H-imidazol-1-yl]-6-heptenoic acid, methyl ester (0.061 g) as a brown gum. δ($CDCl_3$) values include 1.40(d, J6 Hz,$(CH_3)_2CH$), 1.50(s, $OC(CH_3)_3$), 2.45(d,J6 Hz, $CH_2CO_2Me$), 3.14(septet, J6 Hz,$(CH_3)_2CH$), 3.73(s,$CO_2Me$), 4.09–4.25(m,$CH(OH)CH_2CO_2Me$), 4.38–4.49(m,CH=CHCH(OH)), 5.31(dd,J14 and 7 Hz,NCH=CH), 6.42(bs,NH), 6.66(dd,J14 and 1 Hz,NCH=CH), 6.92,7.08,7.09, 7.35 and 6.85–7.50(bd,J8 Hz,t,J9 Hz,tJ9 Hz,bs, and m aromatic protons). From (±)-(E)-7-[4-(3(((1,1-dimethylethoxy)carbonyl)amino)phenyl)-5-(4-fluorophenyl)-2-(1-methylethyl)-1H-imidazol-1-yl]-5-hydroxy-3-oxo-6-heptenoic acid, methyl ester (0.065 g).

EXAMPLE 14

(±)-Erythro-(E)-3,5-dihydroxy-7-[4-(3-(((1,1-dimethylethoxy)carbonyl)methylamino)phenyl)-5-(4-fluorophenyl)-2-(1-methylethyl)-1H-imidazol-1-yl]-6-heptenoic acid, methyl ester (4.85 g) $R_f$ 0.25 System A (3:1)); δ($CDCl_3$) values include 1.39–1.43 (bs, $CH_3)_2CH$ and $OC(CH_3)_3$), 2.45 (d,J6 Hz,$CH_2CO_2CH_3$), 3.13 (s,$CH_3N$), 3.73 (s,$CO_2CH_3$), 4.35–4.45 (m,NCH=CHCH(OH)), 5.31 (dd,J14 and 6 Hz,NCH=CH), 6.66 (dd,J14 and 1 Hz,NCH=CH), 6.97–7.35 (m,aromatic protons) From (±)-(E)-7-[4-(3-(((1,1-dimethylethoxy)carbonyl)methylamino)phenyl)-5-(4-fluorophenyl)-2-(1-methylethyl)-1H-imidazol-1-yl]-5-hydroxy-3-oxo-6-heptenoic acid, methyl ester (7.65 g)

EXAMPLE 15

Methyl(±)-(E)-erythro-3,5-dihydroxy-7-[4-[3-[((((1,1-(dimethyl) ethoxy)carbonyl)methylamino)methyl)phenyl]]-5-(4-fluorophenyl)-2-(1-methylethyl)-1H-imidazol-1-yl]-6-heptenoate (160 mg) δ($CDCl_3$) values include 1.42 (d,J6 Hz, $(CH_3)_2CH$), 1.48 (s, $(CH_3)_3C$), 2.48 (m,$CH_2CO_2Me$), 2.6–2.78 (m,$NCH_3$), 3.16 (septet,J6 Hz, $CH(CH_3)_2$), 3.73 (s,$CO_2CH_3$), 4.32 (s,$CH_2N$), 4.45 (m,CHOH), 5.31 (dd,J15 and 6 Hz,NCH=CH), 6.68 (d,J15 Hz,NCH=CH), 6.95–7.45 (m,aromatic protons). From methyl (±)-(E)-7-[4-[3-[((((1,1-(dimethyl)ethoxy)carbonyl)methylamino)methyl)phenyl]]-5-(4-fluorophenyl)-2-(1-methylethyl)-1H-imidazol-1-yl]-5-hydroxy-3-oxo-6-heptenoate (130 mg).

EXAMPLE 16

(±)-Erythro-(E)-7-[4-(3-cyclohexylaminophenyl)-5-(4-fluorophenyl)-2-(1-methylethyl)-1H-imidazol-1-yl]-3,5-dihydroxy-6-heptenoic acid, methyl ester To a stirred solution of (±)-erythro-(E)-7-[4-(3-aminophenyl)-5-(4-fluorophenyl)-2-(1-methylethyl)-1H-imidazol-1-yl]-3,5-dihydroxy-6-heptenoic acid methyl ester (0.030 g) in dry THF (1 ml) was added 3 Å molecular sieves (activated) and cyclohexanone (0.0067 ml). The mixture was stirred at room temperature under $N_2$ for 19 h, after which a further portion of cyclohexanone (1.00 ml) was added. The mixture was stirred for a further six days, after which time sodium borohydride (0.73 g) as a solution in methanol (10 ml) was added. The mixture was stirred at room temperature for 5 h, then diluted with acetone (5 ml). The mixture was filtered and the residue washed with acetone and ether. The filtrate was concentrated to a colourless translucent solution which was dissolved in 2M aqueous hydrochloric acid (50 ml) and the resultant solution washed with ether (3×30 ml). The aqueous phase was then basified using saturated aqueous sodium bicarbonate solution, and the solution extracted with ethyl acetate (3×75 ml). The organic extracts were combined, dried and concentrated to give a colourless film (0.14 g). This material was purified by CC eluting with ethyl acetate to yield the title compound (0.013 g) as a colourless film. δ($CDCl_3$) values include 1.40(d,J6 Hz,$CH(CH_3)_2$), 2.45(d,J6 Hz,$CH_2CO_2CH_3$), 2.89–3.04(m,$NHCHC_3H_{10}$), 3.14(septet,J6 Hz,$CH(CH_3)_2$), 3.73(s,$CH_2CO_2CH_3$), 4.08–4.22(m,$CH(OH)CH_2CO_2CH_3$), 4.35–4.47(m,NCH=CHCH(OH)), 5.29(dd,J14 and 7 Hz,NCH=CH), 6.62(s,C-2 proton of 3-aminophenyl), 6.65(d,J14 Hz,NCH=CH), 6.39 and 6.77(2d,J8 Hz, C-4 and C-6 protons of 3-aminophenyl), 7.00(t,J8 Hz, C-5 proton of 3-aminophenyl). 7.07(t,J9 Hz,C-3 and C-5 protons of 4-fluorophenyl).

EXAMPLE 17

(±)-Erythro-(E)-7-[4-(3-diethylaminophenyl)-5-(4-fluorophenyl)-2-(1-methylethyl)-1H-imidazol-1-yl]-3,5-dihydroxy-6-heptenoic acid, methyl ester To a stirred solution of (±)-erythro-(E)-7-[4-(3-aminophenyl)-5-(4-fluorophenyl)-2-(1-methylethyl)-1H-imidazol-1-yl]-3,5-dihydroxy-6-heptenoic acid, methyl ester (0.030 g) in acetonitrile (1 ml) under $N_2$ was added ethyl iodide (0.051 ml) and the mixture stirred at room temperature for 19 h. A further portion of ethyl iodide (0.051 ml) was added and the mixture heated at reflux for 3 h. After this time, acetonitrile (0.5 ml) and a further portion of ethyl iodide (0.051 ml) was added and the reflux continued for an additional 26 h. The mixture was allowed to cool, and preparative t.l.c eluting twice with System A (3:1) and once with ethyl acetate, yielded a yellow-brown gum (0.006 g) and a yellow-brown gum (0.010 g). These mixtures were subjected further to preparative t.l.c. eluting with System A (3:1) to yield the title compounds (0.003 g) as a yellow gum. δ($CDCl_3$) values include 1.00(t,J7 Hz,$N(CH_2CH_3)_2$), 1.43(d,J6 Hz,$CH(CH_3)_2$), 2.46(d,J6 Hz,$CH_2CO_2Me$), 3.19(q,J7 Hz,$N(CH_2CH_3)_2$), 3.73(s,$CH_2CO_2Me$), 4.10–4.24(m,$CH(OH)CH_2CO_2Me$), 4.39–4.48(m,NCH=CHCH(OH)), 5.35(dd,J14.

EXAMPLE 18

(±)-Erythro-(E)-3,5-dihydroxy-7-[5-(4-fluorophenyl)-2-(1-methylethyl)-4-(3-(piperidin-1-yl)phenyl-1H-imidazol-1-yl]-6-heptenoic acid, methyl ester. To a stirred solution of (±)-erythro-(E)-7-[4-(3-aminophenyl)-5-(4-fluorophenyl)-2-(1-methylethyl)-1H-imidazol-1-yl]-3,5-dihydroxy-6-heptenoic acid, methyl ester (0.030 g) in acetonitrile (1 ml) was added 1,5-dibromopentane (0.009 ml) and the mixture stirred for nineteen days. A further portion of 1,5-dibromopentane (0.005 ml) was added and the mixture stirred for an additional sixteen days. The reaction mixture was purified directly by preparative tlc eluting with ethyl acetate to yield the title compound (0.011 g) as a brown gum. $R_f$ 0.59 (ethyl acetate); δ($CDCl_3$) values include 1.40 (d,J7 Hz, $(CH_3)_2CH$), 2.44 (d,J6 Hz, $CH_2CO_2CH_3$), 3.12 (septet,J7 Hz, $(CH_3)_2CH$), 3.73 (s,$CO_2CH_3$), 4.38–4.48 (m,NCH=CHCH(OH), 5.33 (dd,J15 and 6 Hz,NCH=CH), 6.60–7.30 (m,aromatic protons).

EXAMPLE 19

(±)-Erythro-(E)-3,5-Dihydroxy-7-[5-(4-fluorophenyl)-4-(3-methylaminophenyl)-2-(1-methylethyl)-1H-imidazol-1-yl]-6-heptenoic acid, methyl ester Trifluoroacetic acid (25 ml) was added to a stirred solution of (±)-erythro-(E)-3,5-dihydroxy-7-[4-(3-(((1,1-dimethylethoxy) carbonyl) methylamino) phenyl)-5-(4-fluorophenyl)-2-(1-methylethyl)-1H-imidazol-1-yl]-6-heptenoic acid, methyl ester (1.046 g) in anisole (9 ml) at 0°. After 0.5 h, ethyl acetate (150 ml) was added and the reaction quenched with saturated aqueous sodium hydrogen carbonate solution and solid sodium hydrogen carbonate until the aqueous phase was pH8. The aqueous phase was extracted with ethyl acetate (2×300 ml) and the combined organic phases dried, evaporated and purified by CC eluting with System A (1:1), (17:3), (1:0)) then System C (9:1) to give the title compounds (0.777 g) as a pale yellow foam. $R_f$ 0.12 (System A, (4:1)); δ($CDCl_3$) details as for Example 10.

EXAMPLE 20

Sodium (±)-erythro-(E)-3,5-dihydroxy-7-[5-(4-fluorophenyl)-4-(3-methylaminophenyl)-2-(1-methylethyl)-1H-imidazol-1-yl]-6-heptenoate An impure sample of (±)-erythro-(E)-3,5-dihydroxy-7-[5-(4-fluorophenyl)-4-(3-methylaminophenyl)-2-(1-methylethyl)-1H-imidazol-1-yl]-6-heptenoic acid, methyl ester (0.010 g) was dissolved in distilled THF (0.5 ml). 0.1N Aqueous sodium hydroxide (0.15 ml) was added with stirring. The reaction mixture was evaporated to dryness and the residue was partiotioned between water (5 ml) and cyclohexane (5 ml). The aqueous phase was separated off, filtered, and freeze-dried to give the title compound (0.009 g) as a pale yellow solid. $R_f$ 0.20 (chloroform-methanol-concentrated aqueous ammonia (80:30:10)), δ($D_2O$) values include 1.34(d,J7 Hz, $(CH_3)_2CH$)), 2.25(d,J6 Hz,$CH_2CO_2Me$), 2.56(s,$NCH_3$), 3.28(septet, J6 Hz, $(CH_3)_2CH$), 3.56–3.74(m,CH(OH)$CH_2CO_2Me$), 4.28–4.41(m,CH=CHCH(OH), 5.56 (dd, J14 & 7 Hz,NCH=CH), 6.76(d,J14 Hz,NCH=CH), 6.63–6.76, 6.86, 7.16, 7.19, 7.26–7.38(m,d,J8 Hz,t, J8 Hz, t, J9 Hz,m, aromatic protons). This sample contained 10% of an impurity.

Similarly prepared:

EXAMPLE 21

Sodium (_) erythro-(E)-3,5-dihydroxy-7-[5-(4-fluorophenyl)-2-(1-methylethyl)-4-[(3-methylthio)phenyl]-1-H-imidazol-1-yl]-6-heptenoate(26 mg); λmax ($H_2O$ 252.8 nm (ε20,467); δ($D_2O$) 1.35 (d, J=6 Hz, $Me_2CH$), ca.1.4–1.84 (m, CH(OH)$CH_2$CH(OH)), 2.25 (d, J=6 Hz, $CH_2CO_2Na$), 2.23 (s, MeS), 3.28 (septet, J=6 Hz, $Me_2CH$), 3.58–3.72 (m, $CH_2$CH(OH)$CH_2CO_2Na$), 4.28–4.41 (m, CH=CH.CH) 5.53 (dd, J=14 Hz, 7 Hz, CH=CH.CH), 6.75 (d, J=14 Hz, NCH=CH), 7.10–7.40 (m, aromatic protons).

From methyl (±)-erythro-(E)-3,5-dihydroxy-7-[5-(4-fluorophenyl)-2-(1-methylethyl)-4-[(3-methylthio)-phenyl]-1H-imidazol-1-yl]-6-heptenoate (0.023 g).

EXAMPLE 22

Sodium (±)-erythro-(E)-3,5-dihydroxy-7-[4-(4fluorophenyl)-2-(1-methylethyl)-5-[(3-methylthio)-phenyl]-1H-imidazol-1-yl]-6-heptenoate (20 mg) as a cream coloured solid. λmax ($H_2O$) 255.8 mm (ε19,200), 272.4 mm (inf) (ε11,350); δ($D_2O$) 1.34 (d, J=7 Hz, $Me_2CH$), ca.1.35–1.55 (m, CH(OH)$CH_2$CH(OH)), 2.19–2.28 (m, $CH_2CO_2Na$) 2.39 (s, MeS), 3.27 (septet, J=7 Hz, $Me_2CH$), 3.51–3.64 (m, $CH_2$CH(OH)$CH_2CO_2Me$), 4.28–4.41 (m, CH=CH.CH) 5.52 (dd, J=15 Hz, 7 Hz, CH=CH.CH) 6.76 (d, J=15 Hz, N.CH=CH), 6.98 and 6.99–7.38 (t, J=9 Hz and m, aromatic protons). From methyl (±)-erythro-(E)-3,5-dihydroxy-7-[4-(4-fluorophenyl)-2-(1-methylethyl)-5-[(3-methylthio)phenyl]-1H-imidazol-1-yl]-6-heptenoate (17 mg).

EXAMPLE 23

Sodium (±)-erythro-(E)-3,5-dihydroxy-7-[5-(4-fluorophenyl)-2-(1-methylethyl)-4-[(3-methylsulphonyl)phenyl]-1H-imidazol-1-yl]-6-heptenoate (24 mg); λmax ($H_2O$), 226.0 nm (inf) (ε16,000), 279.4 nm (ε10,450); δ($D_2O$) 1.36 (d, J=7.5 Hz, $Me_2CH$), ca. 1.38–1.84 (m, CH(OH)$CH_2$CH(OH)), 2.25 (d, J=6 Hz, $CH_2CO_2Na$), 3.29(septet, J=7.5 Hz, $Me_2CH$), 3.59–3.73 (m, $CH_2$CH(OH)$CH_2CO_2Na$) 4.29–4.42 (m, CH=CH.CH), 5.59 (dd, J=15 Hz, 7.5 Hz, CH=CH.CH), 6.78 (d, J=15 Hz, NCH=CH), 7.21, 7.31, 7.56 and 7.72–7.82 (t, J=9 Hz, dd, J=8 Hz, 6 Hz, d, J=7 Hz and m, aromatic protons). From methyl (±)-erythro-(E)-3,5-dihydroxy-7-[5-(4-fluorophenyl)-2-(1-methylethyl)-4-[(3-methylsulphonyl)phenyl]-1H-imidazol-1-yl]-6-heptonate (29 mg).

EXAMPLE 24

Sodium (±)-erythro-(E)-3,5-dihydroxy-7-[4-(4-fluorophenyl)-2-(1-methylethyl)-5-[(3-methylsulphonyl)phenyl]-1H-imidazol-1-yl]-6-heptenoate (18 mg), as a white solid $\lambda_{max}$ ($H_2O$) 228.4 nm (inf) (ε14,865), 266.2 (inf) (ε7970); δ($D_2O$) 1.35(d,J=6 Hz, $Me_2CH$), ca. 1.42–1.84 (m, CH(OH)$CH_2$CH(OH)), 2.25 (d, J=6 Hz, $CH_2CO_2Na$), 3.19 (s, $MeSO_2$), 3.29 (septet, J=6 Hz, $Me_2CH$), 3.63–3.78 (m, $CH_2$CH(OH)$CH_2CO_2Na$), 4.32–4.40 (m, CH=CH.CH), 5.57(dd,J =15 Hz, 7.5 Hz, CH=CH.CH), 6.85 (d, J=15 Hz, N.CH=CH), 7.03,7.30, 7.62–7.75,7.80 and 7.96(t, J=9 Hz, dd, J=9 Hz, 6 Hz, m,s and d, J=6 Hz, aromatic protons) from methyl (±)-erythro-(E)-3,5-dihydroxy-7-[4-(4-fluorophenyl)-2-(1-methylethyl)-5-[(3-methylsulphonyl)phenyl]-1H-imidazol-1-yl]-6-heptenoate (17 mg).

EXAMPLE 25

Sodium (±)-erythro-(E)-7-[4-(3-aminophenyl)-5-(4-fluorophenyl)-2-(1-methylethyl)-1H-imidazol-1-yl]-3,5-dihydroxy-6-heptenoate (0.030 g); From (±)-Erythro-(E)-7-[4-(3-aminophenyl)-5-(4-fluorophenyl)-2-(1-methylethyl)-1H-imidazol-1-yl]-3,5-dihydroxy-6-heptenoic acid, methyl ester (0.042 g). νmax (Nujol) 1684 $cm^{-1}$ (C=O) δ($D_2O$) values include 1.34(d, J7 Hz, $(CH_3)_2CH$), 2.26 (d, J7 Hz, $CH_2CO_2Me$), 3.27 (septet, J7 Hz, $(CH_3)_2CH$), 3.59–3.73 (m,CH(OH)$CH_2CO_2Na$), 4.28–4.41 (m, CH=CHCH(OH)), 5.53 (dd, J14 and 7 Hz, NCH=CH), 6.74 (d, J14 Hz, NCH=CH), 7.09 7.18,6.65–7.34 (t,J8 Hz, t, J9 Hz,m, aromatic protons).

EXAMPLE 26

Sodium (±)-Erythro-(E)-7-[5-(3-aminophenyl)-4-(4-fluorophenyl)-2-(1-methylethyl)-1H-imidazol-1-yl]-3,5-dihydroxy-6-heptenoate (0.031 g) as a white (hygroscopic) solid. $R_f$ 0.15 (chloroformmethanol-concentrated aqueous ammonia (80:30:10)) δ($D_2O$) values include 1.34(d, J7 Hz, $(CH_3)_2CH$), 2.25(d, J7 Hz, $CH_2CO_2Me$), 3.27(septet, J7 Hz, $(CH_3)_2CH$), 3.53–3.69(m, $CH(OH)CH_2CO_2Me$), 4.29–4.43(m, CH═CHCH(OH)), 5.58(dd, J14 and 7 Hz, NCH═CH), 6.76(d, J14 Hz, NCH═CH), 7.02, 7.23, 6.65–7.45 (t, J9 Hz, t, J8 Hz, and m aromatic protons). From (±)-erythro-(E)-7-[5-(3-aminophenyl)-4-(4-fluorophenyl)-2-(1-methylethyl)-1H-imidazol-1-yl]-3,5-dihydroxy-6-heptenoic acid, methyl ester (0.020 g).

EXAMPLE 27

Sodium (±)-erythro-(E)-3,5-dihydroxy-7-[4-(3-dimethylaminophenyl)-5-(4-fluorophenyl)-2-(1-methylethyl)-1H-imidazol-1-yl]-6-heptanoate (0.006 g); $R_f$ 0.22 (chloroform-methanol-concentrated aqueous ammonia (80:30:10)), δ($D_2O$) values include 1.36(d, J7 Hz), $(CH_3)_2CH$), 2.26(d, J7 Hz, $CH_2CO_2Me$), 2.66(s, $N(CH_3)_2$), 3.29(septet, J7 Hz, $(CH_3)_2CH$), 4.28–4.42(m, CH═CHCH(OH)), 5.56(dd, J14 and 6 Hz, NCH═CH), 6.77(d, J14 Hz, NCH═CH), 6.81–6.92, 6.98, 7.18, 7.17–7.37(m, bd, J8 Hz. t, J9 Hz, m, aromatic protons). From (±)-Erythro-(E)-3,5-dihydroxy-7-[4-(3-dimethylaminophenyl)-5-(4-fluorophenyl)-2-(1-methylethyl)-1H-imidazol-1-yl]-6-heptenoic acid, methyl ester (0.005 g).

EXAMPLE 28

Sodium (±)-erythro-(E)-7-[4-(3-acetamidophenyl)-5-(4-fluorophenyl)-2-(1-methylethyl)-1H-imidazol-1-yl]-3,5-dihydroxy-6-heptenoate (0.003 g); δ($D_2O$) values include 1.54(d, J6 Hz, $(CH_3)_2CH$), 2.27 (s, $CH_3CONH$), 2.44(d, J7 Hz, $CH_2CO_2Na$), 3.47(septet, J6 Hz, $(CH_3)_2CH$), 3.77–3.92(m, $CH(OH)CH_2CO_2Na$), 4.47–4.60(m, CH═CHCH(OH)), 5.75(dd, J14 and 7 Hz, NCH═CH), 6.94(dd, J14 and 1 Hz, NCH═CH), 7.31–7.63(m, aromatic protons). From (±)-erythro-(E)-7-[4-(3-acetamidophenyl)-5-(4-fluorophenyl)-2-(1-methylethyl)-1H-imidazol-1-yl]-3,5-dihydroxy-6-heptenoic acid, methyl ester (0.003 g).

EXAMPLE 29

(±)-Erythro-(E)-7-[4-(3-cyclohexylaminophenyl)-5-(4-fluorophenyl)-2-(1-methylethyl)-1H-imidazol-1-yl]-3,5-dihydroxy-6-heptenoic acid, sodium salt (0.012 g); δ($D_2O$) values include 1.35(d,J6 Hz, $CH(CH_3)_2$), 2.25(d, J6 Hz, $CH_2CO_2Na$), 2.66–2.84(m, $HNCHC_5H_{10}$), 3.27 (septet, J6 Hz, $CH(CH_3)_2$), 3.56–3.76(m, $CH(OH)CH_2CO_2Na$), 4.27–4.42(m, NCH═CHCH(OH)), 5.43–5.63(m, NCH═CH), 6.4–7.4(m, aromatic protons and NCH═CH)). From (±)-erythro-(E)-7-[4-(3-cyclohexylaminophenyl)-5-(4-fluorophenyl)-2-(1-methylethyl)-1H-imidazol-1-yl]-3, 5-dihydroxy-6-heptenoic acid, methyl ester (0.013 g)

EXAMPLE 30

(±)-Erythro-(E)-7-[4-(3-diethylaminophenyl)-5-(4-fluorophenyl)-2-(1-methylethyl)-1H-imidazol-1-yl]-3,5-dihydroxy-6-heptenoic acid, sodium salt (0.006 g); δ($D_2O$) values include 0.97(t, J7 Hz, $N(CH_2CH_3)_2$), 1.46(d,J7 Hz, $CH(CH_3)_2$), 2.36(d,J7 Hz, $CH_2CO_2Na$), 3.14(q,J7 Hz,$N(CH_2CH_3)_2$), 3.39(septet, J7 Hz, $CH(CH_3)_2$), 3.68–3.81(m. $CH(OH)CH_2CO_2Na$), 4.39–4.51(m, NCH═CHCH(OH)). 5.66(dd, J14 and 7 Hz, NCH═CH), 6.78(s, C-2 proton of 3-aminophenyl), 6.86(d,J14 Hz, NCH═CH), 6.92 and 7.15(2d, J8 Hz, C-4 and C-6 protons of 3-aminophenyl). From (±)-erythro-(E)-7-[4-(3-diethylaminophenyl)-5-(4-fluorophenyl)-2-(1-methylethyl)-1H-imidazol-1-yl]-3,5-dihydroxy-6-heptenoic acid, methyl ester (0.0055 g)

EXAMPLE 31

(±)-erythro-(E)-3,5-Dihydroxy-7-[4-(3-(((1,1-dimethylethoxy)carbonyl)amino)phenyl)-5-(4-fluorophenyl)-2-(1-methylethyl)-1H-imidazol-1-yl]6-heptenoic acid, sodium salt (0.026 g); λmax ($H_2O$) 234 (ε25,927), 257 nm (ε12,562); νmax (Nujol), 1703 (C═O) and 1572 $cm^{-1}$ (C═C). From (±)-erythro-(E)-3,5-dihydroxy-7-[4-(3-(((1,1-dimethylethoxy)carbonyl-)amino)phenyl)-5-(4-fluorophenyl)-2-(1-methylethyl)-1H-imidazol-1-yl]-6-heptenoic acid, methyl ester (0.050 g)

EXAMPLE 32

(±)-Erythro-(E)-3,5-dihydroxy-7-[5-(4-fluorophenyl)-2-(1-methylethyl)-4-(3-(piperidin-1-yl)phenyl)-1H-imidazol-1-yl]-6-heptenoic acid, sodium salt (0.011 g); δ($D_2O$), values include 1.34 (d, J7 Hz, $(CH_3)_2CH$), 2.24 (d, J6 Hz, $CH_2CO_2Na$), 3.27 (septet, J7 Hz, $(CH_3)_2CH$), 3.55–3.73 (m, $CH(OH)CH_2CO_2CH_3$), 4.27–4.41 (m, NCH═CHCH(OH)), 5.53 (dd, J15 & 7 Hz, NCH═CH), 6.74 (d, J15 Hz, NCH═CH), 6.90–7.30 (m, aromatic protons). From (±)-erythro-(E)-3,5-dihydroxy-7-[5-(4-fluorophenyl)-2-(1-methylethyl)-4-(3-(piperidin-1-yl)phenyl)-1H-imidazol-1-yl]-6-heptenoic acid, methyl ester (0.011 g)

EXAMPLE 33

Sodium(±)-erythro-(E)-3,5-dihydroxy-7-[5-(4-fluorophenyl)-4-[3-((methylamino)methyl)phenyl]-2-(1-methylethyl)-1H-imidazol-1-yl]-6-heptenoate 17 mg $\gamma_{max}$ (Nujol) 3361 (OH and NH), 1569 (carboxylate) $cm^{-1}$; δ($D_2O$) values include 1.35 (($(CH_3)_2CH$), 2.28 (m, $CH_2CO_2Na$), 2.38 (s, $CH_3N$), 3.29 (septet, J6 Hz, $CH(CH_3)_2$), 3.80 (s, $CH_2N$), 4.35 (m, CHOH), 5.52 (dd, J15 and 6 Hz, NCH═CH), 6.75 (d, J15 Hz, NCH═CH), 7.10–7.38 (m, aromatic protons). From methyl(±)-erythro-(E)-3,5-dihydroxy-7-[5-(4-fluorophenyl)-4-[3-((methylamino)methyl)phenyl]-2-(1-methylethyl)-1H-imidazol-1-yl]-6-heptenoate (19 mg).

PHARMACY EXAMPLES

EXAMPLE 1

Tablets

| | | |
|---|---|---|
| (a) | Compound of the invention | 5.0 mg |
| | Lactose | 95.0 mg |
| | Microcrystalline Cellulose | 90.0 mg |
| | Cross-linked polyvinylpyrrolidone | 8.0 mg |
| | Magnesium Stearate | 2.0 mg |
| | Compression weight | 200.0 mg |

The compound of the invention, microcrystalline cellulose, lactose and cross linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| | | |
|---|---|---|
| (b) | Compound of the invention | 5.0 mg |
| | Lactose | 165.0 mg |
| | Pregelatinised Starch | 20.0 mg |
| | Cross-linked Polyvinylpyrrolidone | 8.0 mg |
| | Magnesium Stearate | 2.0 mg |
| | Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 2

Capsules

| | | |
|---|---|---|
| (a) | Compound of the invention | 5.0 mg |
| | Pregelatinised Starch | 193.0 mg |
| | Magnesium Stearate | 2.0 mg |
| | Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatin capsules of a suitable size.

| | | |
|---|---|---|
| (b) | Compound of the invention | 5.0 mg |
| | Lactose | 177.0 mg |
| | Polyvinylpyrrolidone | 8.0 mg |
| | Cross-linked polyvinylpyrrolidone | 8.0 mg |
| | Magnesium Stearate | 2.0 mg |
| | Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granule. The resultant blend is filled into hard gelatin capsules of a suitable size.

EXAMPLE 3

Syrup

| | | |
|---|---|---|
| (a) | Compound of the invention | 5.0 mg |
| | Hydroxypropyl Methylcellulose | 45.0 mg |
| | Propyl Hydroxybenzoate | 1.5 mg |
| | Butyl Hydroxybenzoate | 0.75 mg |
| | Saccharin Sodium | 5.0 mg |
| | Sorbitol Solution | 1.0 ml |
| | Suitable Buffers | qs |
| | Suitable flavours | qs |
| | Purified Water to | 10. ml |

The hydroxypropyl methylcellulose is dispersed in a portion of hot purified water together with the hydroxybenzoates and the solution is allowed to cool to room temperature. The saccharin sodium, flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

We claim:

1. A compound of formula (I):

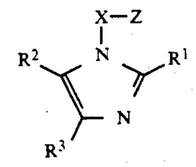

(I)

in which one of the groups $R^1$ or $R^2$ represents a $C_{1-6}$alkyl group optionally substituted by one to three halogen atoms and the other represents a phenyl ring optionally substituted by one to five substituents selected from halogen atoms and hydroxyl, $C_{1-3}$alkyl, $C_{1-3}$alkoxy, $S(O)_nC_{1-3}$alkyl, $(CH_2)_mNR^aR^b$, $(CH_2)_mNR^cCOR^d$ and trifluoromethyl groups, or a phenyl ring monosubstituted by a pyrrolidino, piperidino or hexamethylenimino ring;

$R^3$ represents a phenyl ring optionally substituted by one to five substituents selected from halogen atoms and hydroxyl, $C_{1-3}$alkyl, $C_{1-3}$alkoxy, $S(O)_n$-$C_{1-3}$alkyl, $(CH_2)_mNR^aR^b$, $(CH_2)_mNR^cCOR^d$ and trifluoromethyl groups, or a phenyl ring monosubstituted by a pyrrolidino, piperidino or hexamethylenimino ring, with the proviso that at least one of the groups $R^1$, $R^2$ and $R^3$ contains an $S(O)_nC_{1-3}$alkyl, $(CH_2)_mNR^aR^b$, $(CH_2)_mNR^cCOR^d$, pyrrolidino, piperidino or hexamethylenimino substituent;

X represents —CH=CH—; and

Z represents

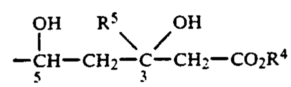 or (a)

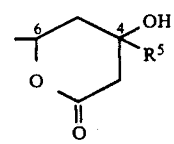

(b)

m represents zero, 1, 2, 3 or 4;

n represents zero, 1 or 2;

$R^a$ and $R^b$, which may be the same or different, each represent a hydrogen atom, a $C_{1-4}$alkyl group, or a saturated monocyclic 5 to 7 membered ring;

$R^c$ represents a hydrogen atom or a $C_{1-4}$alkyl group;

$R^d$ represents a hydrogen atom, a $C_{1-4}$alkyl group or a $C_{1-4}$alkoxy group;

$R^4$ represents a hydrogen atom or a physiologically acceptable cation, or the group $—CO_2R^4$ represents a physiologically acceptable and metabolically labile ester;

$R^5$ represents a hydrogen atom or a $C_{1-3}$alkyl group;

or a physiologically acceptable solvate thereof, or a physiologically acceptable acid addition salt thereof when $R^4$ represents hydrogen or the group $—CO_2R^4$ represents a physiologically acceptable and metabolically labile ester group when Z is (a), or a quaternary ammonium derivative thereof when a group $(CH_2)_mNR^aR^b$ or a pyrrolidino, piperidino or hexamethylenimino group is present.

2. A compound as claimed in claim 1 in which $R^5$ represents a hydrogen atom.

3. A compound as claimed in claim 1 in which $R^1$ represents an isopropyl group.

4. A compound as claimed in claim 1 in which $R^2$ represents a substituted phenyl group and $R^3$ represents a phenyl group mono-substituted in the 3-position by a group $S(O)_nC_{1-3}$alkyl, $(CH_2)_mNR^aR^b$ or $(CH_2)_mNR^cCOR^d$ or by a pyrrolidino, piperidino or hexamethylenimino ring.

5. A compound as claimed in claim 4 in which $R^2$ represents a 4-fluorophenyl group.

6. A compound as claimed in claim 1 in which the group X is in the (E) configuration.

7. Erythro-(E)-3,5-dihydroxy-7-[5-(4-fluorophenyl)-4-(3-methylaminophenyl)-2-(1-methylethyl)-1H-imidazol-1-yl]-6-heptenoic acid or a physiologically acceptable salt, physiologically acceptable and metabolically labile ester or a physiologically acceptable solvate thereof.

8. Trans-(E)-6-[2-[5-(4-fluorophenyl)-4-(3-methylaminophenyl)-2-(1-methylethyl)-1H-imidazol-1-yl]ethenyl]-4-hydroxy-tetrahydro-2H-pyran-2-one or a physiologically acceptable acid addition salt or physiologically acceptable solvate thereof.

9. A compound as claimed in claim 1 as a mixture of enantiomers.

10. The 3R, 5S enantiomer of a compound of claim 1.

11. Sodium (3R, 5S, E)-3,5-dihydroxy-7-[5-(4-fluorophenyl)-4-(3-methylaminophenyl)-2-(1-methylethyl)-1H-imidazol-1-yl]-6-heptenoate.

12. A pharmaceutical formulation comprising an effective dosage of a compound as claimed in claim 1 or a physiologically acceptable derivative thereof together with one or more physiologically acceptable carriers therefor.

13. A method for the treatment of a disease associated with hypercholesterolemia and hyperlipoproteinemia comprising administration of a compound of formula I as defined in claim 1 or a physiologically acceptable derivative thereof.

* * * * *